(12) United States Patent
Fischer et al.

(10) Patent No.: US 9,125,714 B2
(45) Date of Patent: Sep. 8, 2015

(54) ELECTRIC TOOTHBRUSH, AND TRANSMISSION FOR AN ELECTRIC TOOTHBRUSH

(71) Applicant: TRISA HOLDING AG, Triengen (CH)

(72) Inventors: Franz Fischer, Triengen (CH); Armin Baertschi, Winznau (CH); Christian Hilfiker, Triengen (CH)

(73) Assignee: TRISA HOLDING AG, Triengen (CH)

( * ) Notice: Subject to any disclaimer, the term of this patent is extended or adjusted under 35 U.S.C. 154(b) by 0 days.

(21) Appl. No.: 13/678,724

(22) Filed: Nov. 16, 2012

(65) Prior Publication Data

US 2013/0097789 A1   Apr. 25, 2013

Related U.S. Application Data

(63) Continuation of application No. 12/227,862, filed as application No. PCT/EP2007/004127 on May 10, 2007, now Pat. No. 8,365,335.

(30) Foreign Application Priority Data

Sep. 29, 2006   (EP) .................................... 06020546

(51) Int. Cl.
  *A61C 17/22*   (2006.01)
  *A61C 17/34*   (2006.01)
  *A46B 9/04*   (2006.01)

(52) U.S. Cl.
  CPC .............. *A61C 17/3409* (2013.01); *A46B 9/04* (2013.01); *A61C 17/34* (2013.01); *A61C 17/349* (2013.01); *A61C 17/3472* (2013.01); *A61C 17/3418* (2013.01); *A61C 17/3427* (2013.01); *A61C 17/3436* (2013.01); *A61C 17/3445* (2013.01)

(58) Field of Classification Search
  CPC ........... A61C 17/3409; A61C 17/3418; A61C 17/3427
  USPC .............................. 15/22.1, 22.2, 22.4, 23, 28
  See application file for complete search history.

(56) References Cited

U.S. PATENT DOCUMENTS

| 3,104,409 A |   | 9/1963 | West |
| 3,187,360 A | * | 6/1965 | Spohr ........................... 15/22.1 |
| 3,435,477 A |   | 4/1969 | Moyer |
| 3,489,936 A |   | 1/1970 | Boyles |
| 3,524,088 A |   | 8/1970 | Ryckman, Jr. |
| 4,710,995 A |   | 12/1987 | Joyashiki et al. |
| 5,321,865 A |   | 6/1994 | Kaeser |

(Continued)

FOREIGN PATENT DOCUMENTS

| CH | 688 537 A5 | 11/1997 |
| DE | 1532781 | 3/1970 |

(Continued)

*Primary Examiner* — Monica Carter
*Assistant Examiner* — Michael Jennings
(74) *Attorney, Agent, or Firm* — Oliff PLC

(57) ABSTRACT

The transmission according to the invention for an electric toothbrush serves for the transmission and reforming of a rotational movement provided by an electric motor into a particularly careful and effective cleaning movement of a cleaning element. The ratio of the distance between the longitudinal mid-axis of an output shaft and the longitudinal mid-axis of a drive shaft of the transmission and of the distance between the longitudinal mid-axis of a shaft driving a cam of the transmission and the longitudinal mid-axis of the cam amounts to at least 10:1.

24 Claims, 15 Drawing Sheets

(56) References Cited

U.S. PATENT DOCUMENTS

| | | | |
|---|---|---|---|
| 5,381,576 A * | 1/1995 | Hwang | 15/22.1 |
| 5,504,959 A | 4/1996 | Yukawa et al. | |
| 5,850,655 A * | 12/1998 | Gocking et al. | 15/28 |
| 6,463,615 B1 * | 10/2002 | Gruber et al. | 15/22.1 |
| 6,575,924 B2 | 6/2003 | Wevers et al. | |
| 6,581,233 B1 | 6/2003 | Cheng | |
| 6,760,945 B2 * | 7/2004 | Ferber et al. | 15/22.2 |
| 6,779,215 B2 * | 8/2004 | Hartman et al. | 15/22.1 |
| 6,792,640 B2 * | 9/2004 | Lev | 15/28 |
| 6,799,346 B2 * | 10/2004 | Jeng et al. | 15/28 |
| 6,813,794 B2 * | 11/2004 | Weng | 15/22.4 |
| 6,895,625 B2 * | 5/2005 | Lev et al. | 15/28 |
| 6,920,660 B2 * | 7/2005 | Lam | 15/22.1 |
| 6,964,076 B2 * | 11/2005 | Zhuan | 15/22.2 |
| 7,067,945 B2 * | 6/2006 | Grez et al. | 310/50 |
| 7,360,269 B2 | 4/2008 | Cobabe et al. | |
| 7,430,778 B2 * | 10/2008 | Gatzemeyer et al. | 15/22.2 |
| 7,640,615 B2 * | 1/2010 | Blaustein et al. | 15/22.2 |
| 2002/0174498 A1 * | 11/2002 | Li | 15/28 |
| 2003/0000031 A1 | 1/2003 | Zhuan | |
| 2003/0126700 A1 * | 7/2003 | Jeng et al. | 15/28 |
| 2003/0194678 A1 | 10/2003 | Viltro et al. | |
| 2004/0016068 A1 | 1/2004 | Lee | |
| 2004/0016069 A1 | 1/2004 | Lee | |
| 2004/0019987 A1 * | 2/2004 | Chu | 15/22.1 |
| 2004/0045106 A1 * | 3/2004 | Lam | 15/22.1 |
| 2004/0074026 A1 | 4/2004 | Blaustein et al. | |
| 2004/0123409 A1 * | 7/2004 | Dickie | 15/22.1 |
| 2004/0158944 A1 | 8/2004 | Fattori | |
| 2004/0255409 A1 | 12/2004 | Hilscher et al. | |
| 2005/0055784 A1 * | 3/2005 | Wong | 15/22.1 |
| 2005/0102773 A1 * | 5/2005 | Obermann et al. | 15/4 |
| 2005/0102775 A1 * | 5/2005 | Kressner | 15/22.1 |
| 2005/0144744 A1 * | 7/2005 | Thiess et al. | 15/22.1 |
| 2005/0150067 A1 | 7/2005 | Cobabe et al. | |
| 2005/0199265 A1 | 9/2005 | France et al. | |
| 2005/0278874 A1 | 12/2005 | Blaustein et al. | |
| 2006/0005331 A1 * | 1/2006 | Schutz | 15/22.1 |
| 2006/0010623 A1 * | 1/2006 | Crossman et al. | 15/22.1 |
| 2006/0059638 A1 | 3/2006 | Hegemann et al. | |
| 2006/0096046 A1 * | 5/2006 | Hilscher et al. | 15/22.1 |
| 2006/0101598 A1 * | 5/2006 | Fujimoto et al. | 15/22.2 |
| 2006/0117505 A1 * | 6/2006 | Chan | 15/22.1 |
| 2006/0150350 A1 * | 7/2006 | Pfenniger et al. | 15/22.1 |
| 2006/0168744 A1 * | 8/2006 | Butler et al. | 15/22.1 |
| 2006/0179591 A1 | 8/2006 | Spooner | |
| 2006/0191086 A1 | 8/2006 | Mourad et al. | |
| 2006/0254007 A1 | 11/2006 | Banning | |
| 2007/0011834 A1 | 1/2007 | Shimizu et al. | |
| 2007/0151051 A1 | 7/2007 | Filsouf | |
| 2007/0214587 A1 | 9/2007 | Stoeffler et al. | |
| 2009/0183324 A1 | 7/2009 | Fischer et al. | |

FOREIGN PATENT DOCUMENTS

| | | | |
|---|---|---|---|
| DE | 2024166 | 11/1970 | |
| DE | 42 24 859 A1 | 3/1994 | |
| DE | 197 27 018 A1 | 1/1999 | |
| EP | 1078609 | 11/1999 | |
| EP | 1 532 891 A1 | 5/2005 | |
| EP | 1 639 914 A1 | 3/2006 | |
| FR | 1299056 | 6/1962 | |
| FR | 1 341 439 | 9/1963 | |
| GB | 914844 | 1/1963 | |
| GB | 1 134 158 | 11/1968 | |
| JP | 10066704 A * | 3/1998 | A61C 17/22 |
| WO | WO 92/13499 | 1/1991 | |
| WO | WO 93/15628 | 8/1993 | |
| WO | WO 94/09679 | 5/1994 | |
| WO | WO 03/070122 A1 | 8/2003 | |
| WO | WO 2005060866 A1 * | 7/2005 | A61C 17/22 |

* cited by examiner

Fig. 16 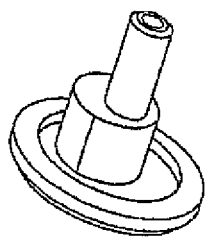 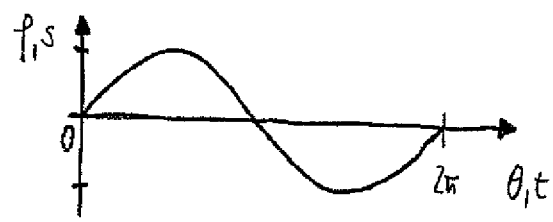
Fig. 17 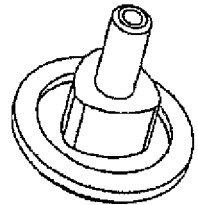 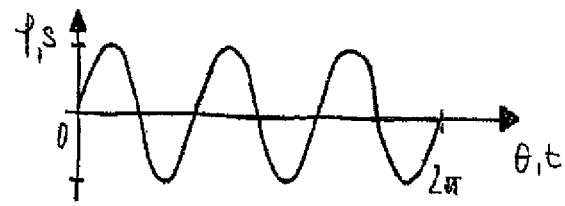
Fig. 18 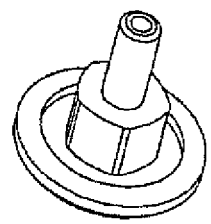 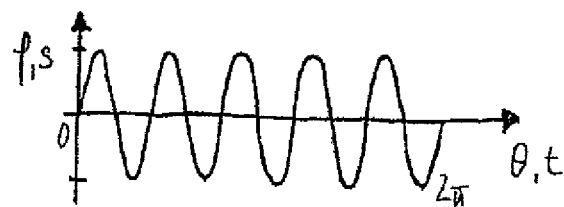
Fig. 19 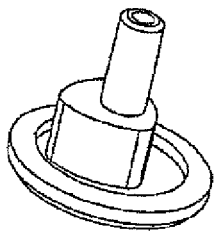 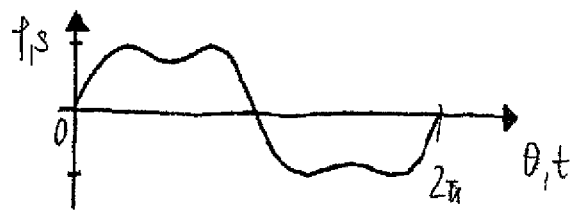
Fig. 20 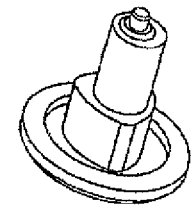 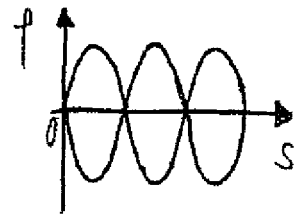

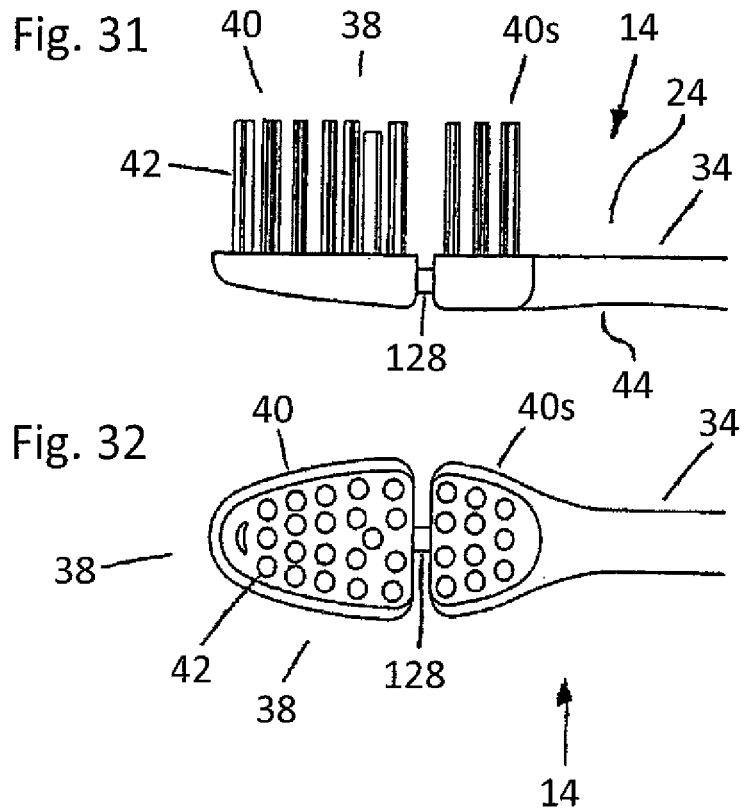
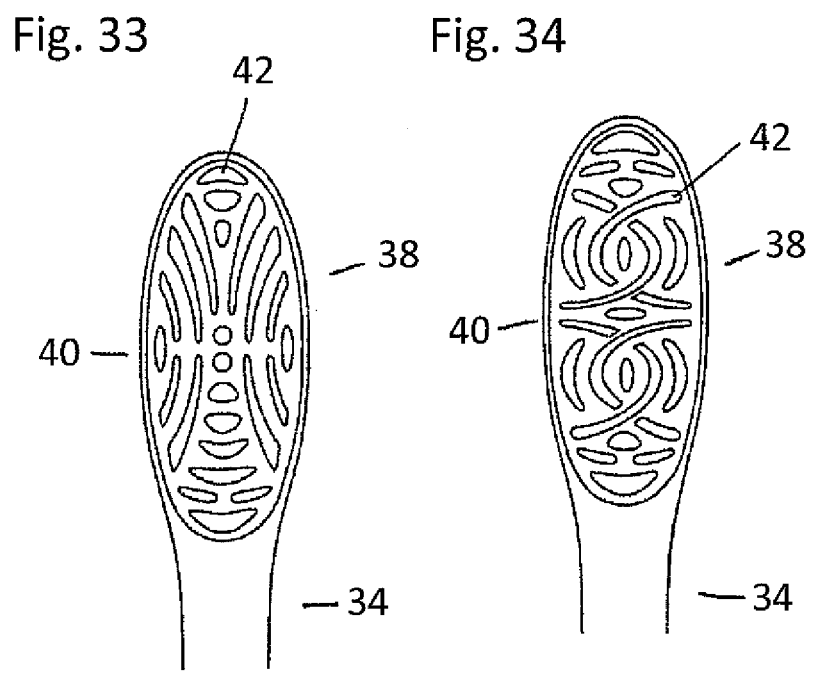

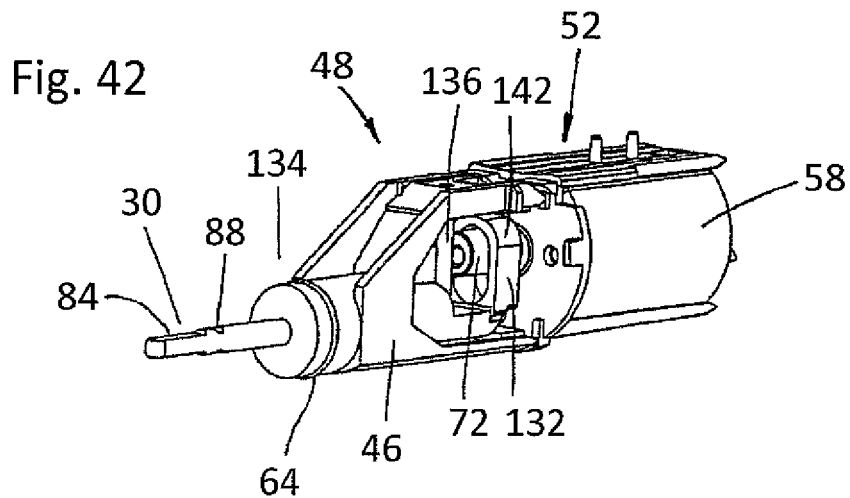
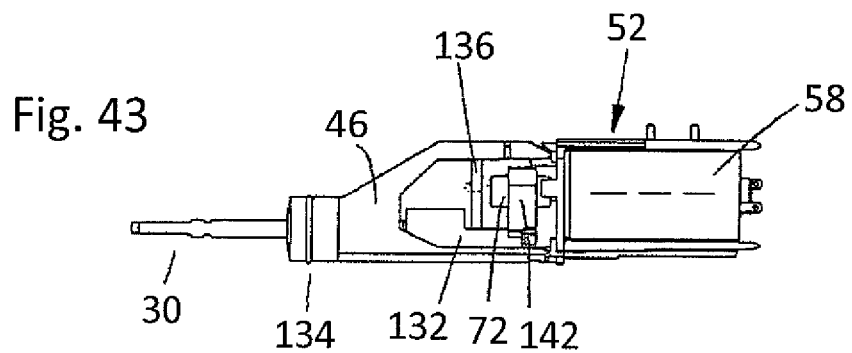
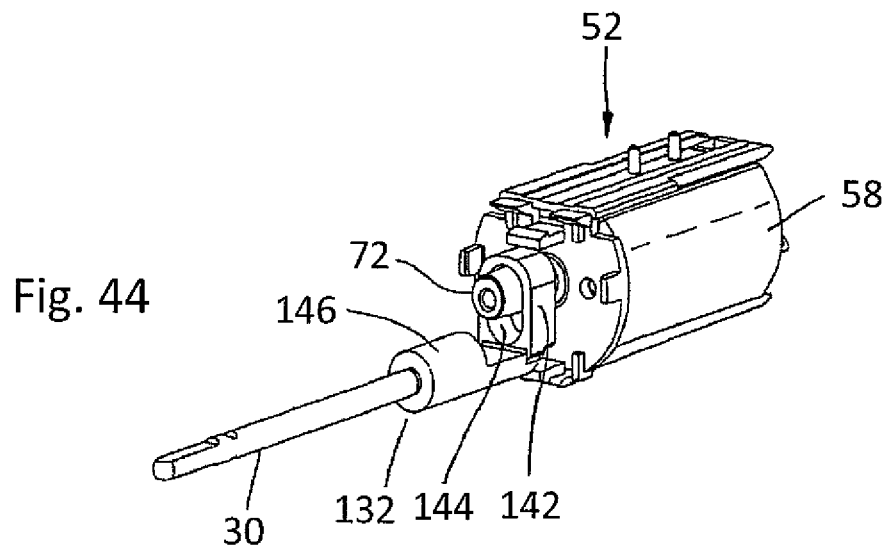

Fig. 49a
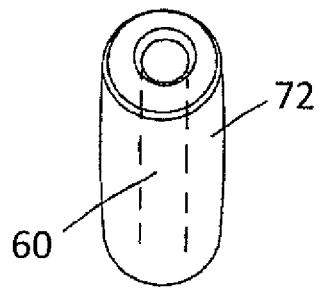
Fig. 49b
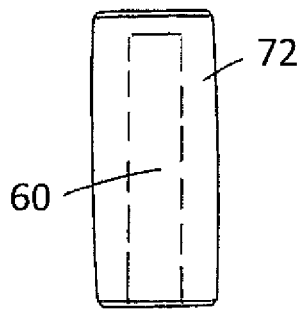
Fig. 50
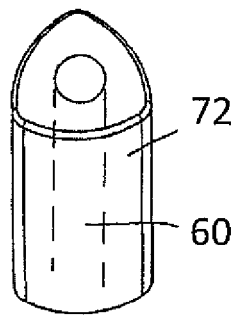
Fig. 51
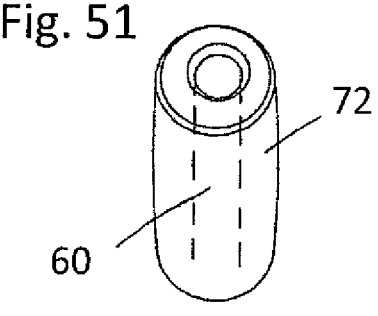
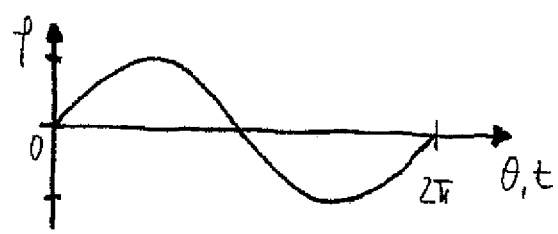
Fig. 52
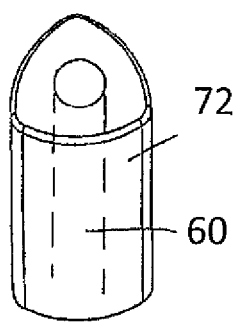
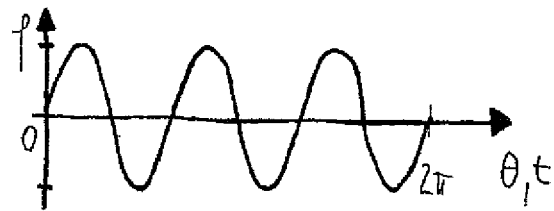

ELECTRIC TOOTHBRUSH, AND TRANSMISSION FOR AN ELECTRIC TOOTHBRUSH

This is a Continuation of application Ser. No. 12/227,862 filed Dec. 1, 2008. The disclosure of the prior application is hereby incorporated by reference herein in its entirety.

The present invention relates to a transmission for an electric toothbrush.

Electrically operated toothbrushes, what are known as electric toothbrushes, which have electric motors for the drive of movements on cleaning elements arranged on them are generally known at the present time. Typically, in this case, the cleaning elements attached to plug-on brushes are moved in a pivoting manner via a reduction gear after a conversion of a rotational movement provided by the electric motor. Depending on the form of movement which the cleaning element executes about an axis assigned to it, a distinction is made between reversibly pivoting, reversibly translational and combined movements which have both reversibly pivoting and reversibly translational movement components.

An electric toothbrush having a reversibly pivotable cleaning element is disclosed, for example, in U.S. Pat. No. 3,104,409. The electric toothbrush described in this has a basic body with an electric motor which is received in the latter and the rotational movement of which is converted by means of a gear into a reversibly pivoting movement of an output shaft. A stick-like plug-on brush is plugged onto the output shaft and in the head-side end region has a cleaning element fitted with bristles. The cleaning element, together with the entire plug-on brush, executes a reversible pivoting movement in the fed state of the electric motor, that is to say in an active operating state, about the output shaft extending essentially parallel to the longitudinal axis of the plug-on brush.

A further electric toothbrush is described in CH 688537. This electric toothbrush, too, has an electric motor which is arranged in a basic body designed as a grip and which, in the active operating state, provides a rotational movement which is converted by means of a gear into a reversibly pivoting movement of an output shaft. In this case, too, a plug-on brush having a bristle-fitted cleaning element arranged on the head region can be plugged onto the basic appliance. An axial prolongation movable in the plug-on brush and having a deflection element converts the pivoting movement of the output shaft into a reversible pivoting movement of the cleaning element as a result of an engagement of the deflection element, at the end region, into a guide slot of a rotary disk carrying the cleaning element. The pivot axis assigned to the cleaning element in this case extends at right angles with respect to the output shaft. The reversible pivoting movement of the rotary disk, designed essentially in the form of a circular disk, which has the cleaning element fastened to it is also designated as a reversibly rotating or reversibly oscillating movement.

An electric toothbrush, in which, in the active operating state, a cleaning element arranged on a plug-on brush executes a reversibly translational to-and-fro movement, is disclosed, for example, in EP-A-1639914. In this case, the entire plug-on brush is moved to and fro, parallel to its longitudinal axis, by means of a slider crank-like gear between a drive shaft in an electric motor and an output-side slider crank rod.

U.S. Pat. No. 5,321,865 describes an oral hygiene device, in particular also an electric toothbrush, of which the cleaning element arranged on a plug-on brush executes, in the active operating state, a combined movement which is composed of a reversible pivoting movement about an output shaft, which runs essentially parallel to the longitudinal axis of the plug-on brush, and of a reversibly translational to-and-fro movement of the output shaft in the direction of the longitudinal axis of the plug-on brush. A gear used in this case possesses two cams which are arranged eccentrically on a gearwheel and which convert the rotational movement, provided by the electric motor when the latter is in the fed state, into the two movement components, on the one hand reversibly pivoting and, on the other hand, translationally to and fro, and transmit them via a pick-up to the output shaft. On account of the specific geometric design of the two cams, the two movement components oscillate at the same frequency, as is predetermined by the gearwheel on which they are arranged fixedly.

Further embodiments of electric toothbrushes with integrated gears are described, for example, in GB 1,134,158, US 2004/0158944, FR 1,341,439 and WO 03/070122.

Additional details regarding the configuration of plug-on brushes and cleaning elements are to be found, inter alia, in the publications DE-A-19727018, DE-A-4228859 and EP-A-1532891.

The object of the present invention, then, is to provide a gear and a movement sequence, associated with this, for the output shaft or the cleaning element, connected to it, of an electric toothbrush and an electric toothbrush having a gear of this type, by means of which it is possible to provide cost-effectively a particularly effective cleaning movement of the cleaning elements which takes care of the gums.

This object is achieved by exemplary transmissions for an electric toothbrush.

The gear according to the invention for an electric toothbrush serves for the transmission and reforming of a rotational movement, provided by an electric motor on a drive shaft, into a movement of an output shaft, which, in turn, is predetermined for driving a movable cleaning element of the electric toothbrush.

For this purpose, the gear has a cam, arranged fixedly in terms of rotation preferably eccentrically with respect to the driving shaft of the gear, and a corresponding pick-up connected fixedly in terms of rotation to the output shaft. So as to injure the gums as little as possible and at the same time achieve a very good cleaning action, the output shaft and the cleaning element connected to it execute a preferably rapid movement, along with low deflection. In order to provide the low deflection required, that is to say the required small deflection angle at the pick-up or at the output shaft, according to the invention, the ratio of the distance from the longitudinal mid-axis of the output shaft to the longitudinal mid-axis of the drive shaft in the region of the pick-up to the distance between the longitudinal mid-axis of the shaft driving the cam and the longitudinal mid-axis of the cam amounts to at least 10:1. The rapidity of movement is achieved, for example, using an electric motor which, in no-load operation, makes available a high rotational speed of between 2000 rev/min and 12 000 rev/min.

The eccentric gear designed thus according to the invention has a relatively simple structural set-up and is equipped with a plurality of structural elements preferably to be processed by the injecting molding method, thus making it possible, overall, to have a particularly cost-effective manufacturing process.

A further object of the present invention is to provide a gear and a movement sequence, associated with it, for the output shaft or the cleaning element, connected to it, of an electric toothbrush and an electric toothbrush having a gear of this type, by means of which it is possible for the manufacturer to adapt the continuous rotational movement provided by an electric motor in one direction of rotation to the desired cleaning movement of a cleaning element of the electric toothbrush more effectively and in a simpler, cost-effective and more flexible way. In this case, the movement of the cleaning element should, preferably in all gear variants, allow a laterally reversible pivoting movement and/or a translational to-and-fro movement in the axial direction of the output shaft.

A further object of the invention is to provide a plug-on brush adapted optimally for the corresponding embodiment of the gear. This refers, in particular, to the design of an advantageous connection between the plug-on brush or the brush head and the output shaft in order to generate an optimal movement sequence. Overall, the invention is to make available the desired movement of the cleaning element via an active chain designed according to the invention, comprising electric motor-gear-output-shaft-plug-on mechanism-plug-on brush-cleaning element-bristles.

The transmission according to the invention, which serves for converting a continuous rotational movement in one direction of rotation, provided by an electric motor on its drive shaft, into a movement for driving a cleaning element, in one embodiment variant is designed as a multistage gear. It possesses at least one drive-side first gear stage and at least one output-side second gear stage, at least one gear stage being designed as a step-down stage and at least one gear stage being designed as a step-up stage. This ensures that the movement transferred by the multistage gear can, in terms of rotational speed and torque, be adapted by the manufacturer in a simple and flexible way, on the one hand, to the specifications of the electric motor and, on the other hand, to the desired movement properties of the cleaning element.

In a further embodiment, the step-up stage of the gear is equipped with a cam and with a cam prolongation, which make it possible to provide both a reversibly pivoting movement component and a reversibly translational movement component or a combination of the two for the output shaft and consequently for the cleaning element. By the geometry and arrangement of the cam and of the cam prolongation being adapted, a multiplicity of novel, particularly effective cleaning movement patterns of the output shaft and therefore also the cleaning element can be generated.

A further object of the present invention is to provide an electric toothbrush having a gear, in which the gear allows a structurally simple, low-noise movement transmission which is as freely predeterminable as possible.

This electric toothbrush according to the invention is equipped with a basic body which shapes a grip and receives an electric motor and a transmission, with a neck adjoining the basic body and with a head which is arranged, opposite the grip, on the neck. A movable cleaning element connected to an output shaft is arranged on the head. The transmission has a cam and a pick-up which is operatively connected to the output shaft. The cam preferably possesses a cross section in the form of a circle or of a rounded n-sided polygon, n being an odd positive number.

In the case of the transmission of a movement of the cam to the pick-up by means of a sliding pick-up, on account of the specific cross-sectional shapes of the cam, step-up ratios equal to and, above all, higher than 1:1 can be implemented. Moreover, the set-up of the transmission is relatively simple, and because of the sliding pick-up there is only a small amount of noise generated in the active operating state.

Some particularly preferred embodiments of the transmission according to the invention and of the electric toothbrush according to the invention are described in detail below with reference to a drawing. In the figures of the drawing, in particular, FIG. 1 shows a perspective view of a basic body, designed as a grip, of an electric toothbrush with a conically tapering end region, from which projects an output shaft, onto which a plug-on brush shown in FIG. 2 can be plugged;

FIG. 16-FIG. 19 show graphical illustrations of the deflection of the output shaft as a function of time and of the angle of rotation of the contrate wheel for various embodiments of cams which are indicated in each case on the left of the graphical illustrations;

FIG. 20 shows a further graphical illustration of the deflection of the output shaft for an embodiment, indicated beside it, of a cam with a cam prolongation, for providing a combined form of movement with a reversibly pivoting and a reversibly translational movement component;

FIG. 31 shows a side view of a further embodiment of the head of the plug-on brush with a cleaning element movable with respect to the neck and with a cleaning element stationary with respect to the neck;

FIG. 32 shows a top view of the top side of the head, shown in FIG. 31, of the plug-on brush;

FIG. 33 shows a top view of the top side of the head of a further embodiment of a plug-on brush with bristle bundles which project from elongately sickle-shaped base areas, the longitudinal extents of which extend approximately in the longitudinal direction of the head;

FIG. 34 shows a top view of the top side of the head of a further embodiment of a plug-on brush with bristle bundles which project from elongately sickle-shaped base areas, the longitudinal extents of which, on the one hand, extend approximately in the longitudinal direction of the head and, on the other hand, extend approximately in the transverse direction of the head;

FIG. 42 shows a perspective view of part of the interior of a further embodiment of an electric toothbrush according to the invention with a single-stage transmission, the cam being directly fastened fixedly in terms of rotation on the drive shaft of the electric motor;

FIG. 43 shows a side view of the interior, shown in FIG. 42, of the electric toothbrush according to the invention;

FIG. 44 shows a perspective view of the interior, shown in FIG. 42 and FIG. 43, of the toothbrush according to the invention, without the internal framework being illustrated;

FIGS. 49a and 49b show respectively a perspective view and a side view of an essentially cylindrical, crowned cam which is intended to be arranged eccentrically with respect to a drive shaft of the electric motor;

FIG. 50 shows a perspective view of a further embodiment of a cam with a rounded, essentially triangular cross-sectional shape;

FIG. 51 shows a graph of the dependence of the deflection angle of the output shaft on the angle of rotation of the drive shaft during one complete rotation of the drive shaft, using the cylindrical cam illustrated in FIG. 49;

FIG. 52 shows a graph of the functional relation between the deflection angle of the output shaft and the angle of rotation of the drive shaft for the cam shown in FIG. 50, having an essentially triangular, rounded cross section;

Figure 1:
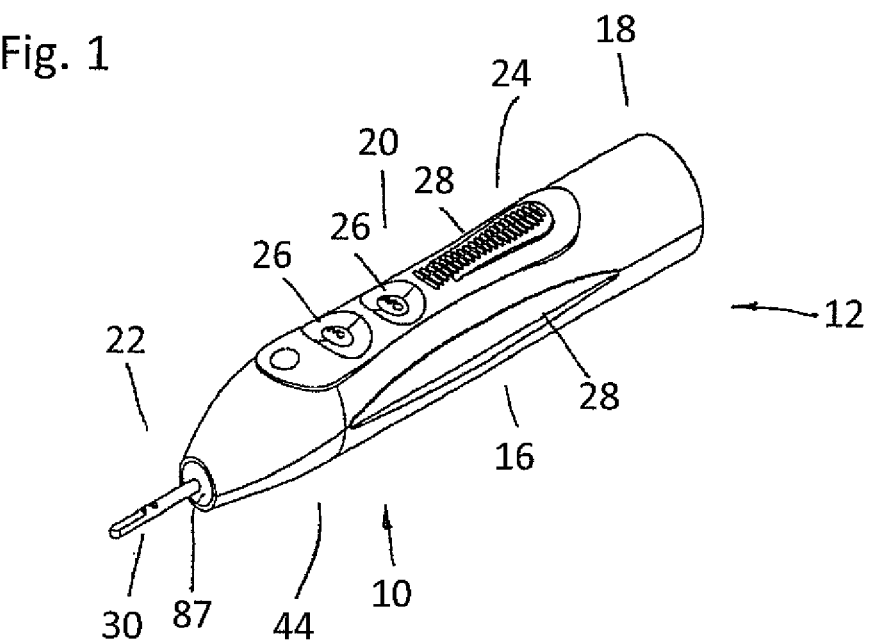
Figure 2:
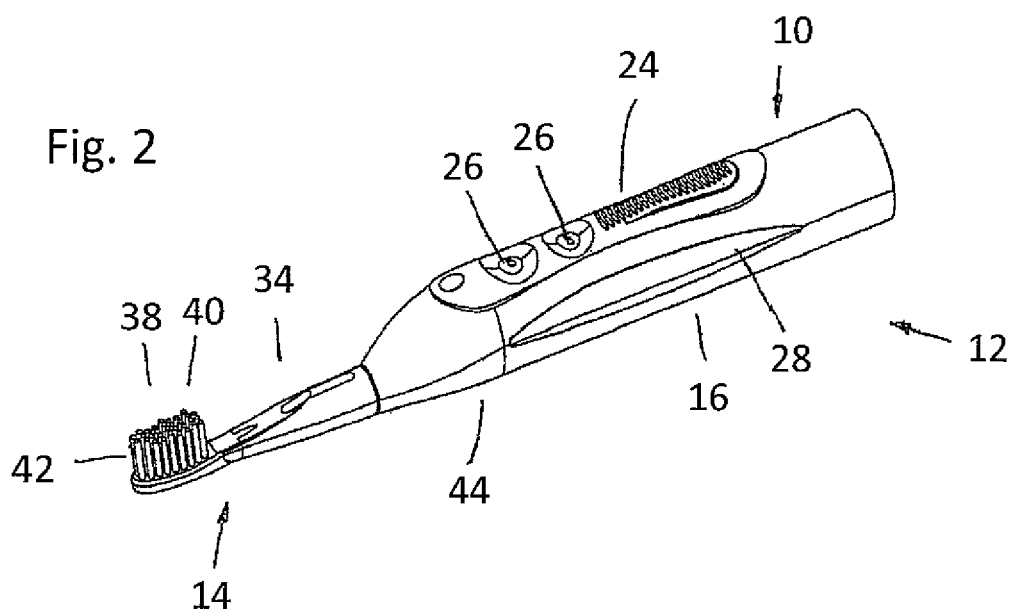
FIG. 2 shows a perspective view of an electric toothbrush with the basic body shown in FIG. 1 and with a plug-on brush plugged onto the output shaft and having a bristle-fitted cleaning element.
Figure 3:
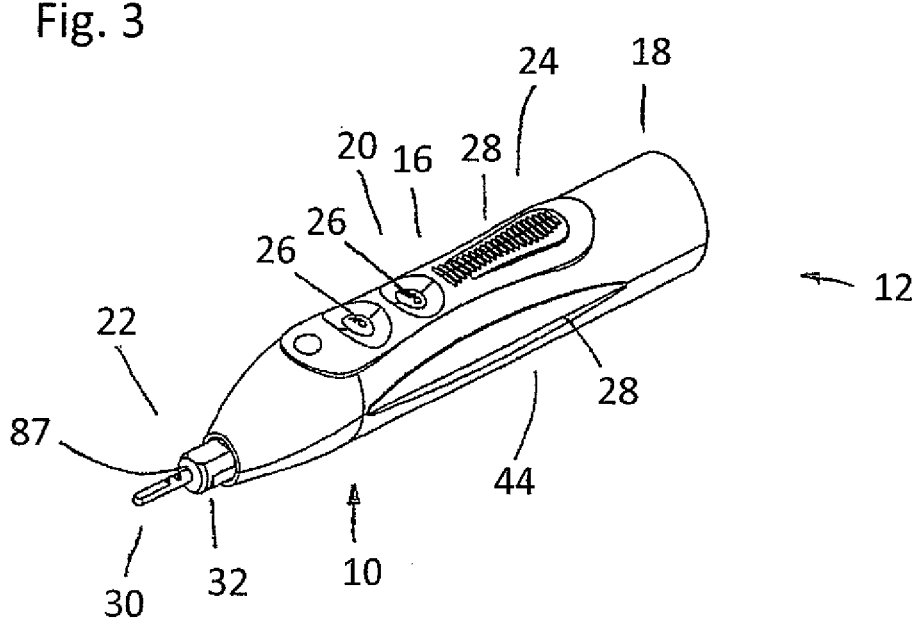
FIG. 3 shows a perspective view of a further embodiment of the basic body of the electric toothbrush according to the invention with a plug-on connection piece, arranged on the output shaft side in the conical end region, for the rotationally fixed reception of a further embodiment of the plug-on brush, shown in FIG. 4.
Figure 4:
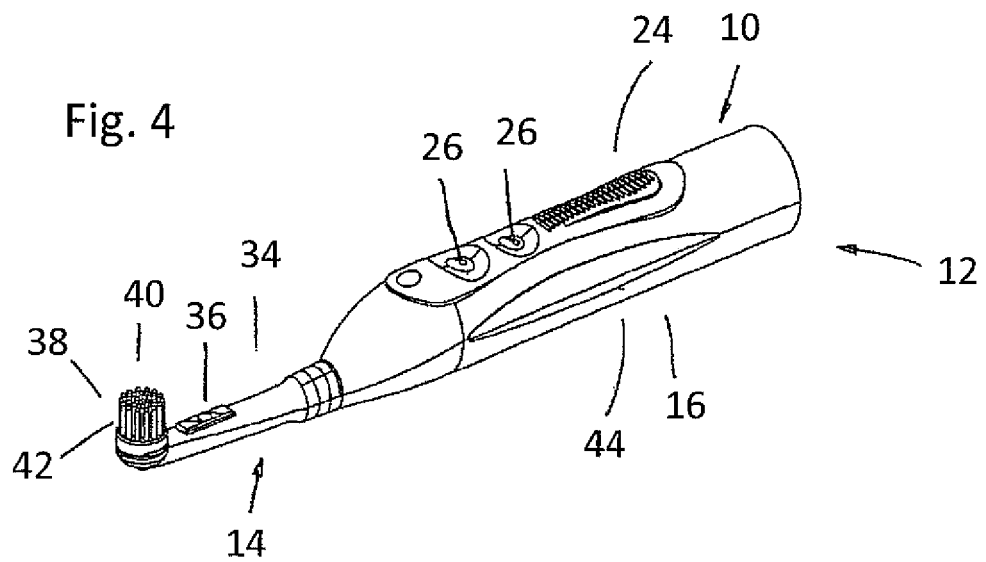
FIG. 4 shows a perspective view of an electric toothbrush according to the invention with the basic body shown in FIG. 3 and with a plugged-on plug-on brush having a reversibly oscillatable cleaning element.

FIGS. 1-4 show basic bodies 10 of electric toothbrushes 12 according to the invention, onto which, for example, plug-on brushes 14 shown in FIG. 2 and FIG. 4 can be plugged. The basic body 10 has an essentially cylinder-like outer contour and forms a grip 16 of the electric toothbrush 12. Along its longitudinal axis, the basic body 10 has, in a lower end region, a standing portion 18, an actuating portion 20 adjoining the latter and a plug-on portion 22 which adjoins the actuating portion 20 and which is arranged at an end region lying opposite the standing portion 18.

The standing portion 18 serves for ensuring that the electric toothbrush 12 stands securely on a fixed base, for example a loading or base station. It comprises a bottom, not shown in FIGS. 1-4, which may, for example, be of planar design, with a standing shape for reception in the loading or base station or with other functional shapes.

The actuating portion 20 extends approximately over two thirds of the overall length of the basic body 10 and, when the electric toothbrush 12 is being used, is surrounded essentially by the inner face of a user's hand. It is equipped on a top side 24 with externally accessible actuating elements 26, formed from soft-elastic material, for the control of operating states of the electric toothbrush 12, for example for switching on and off, for a continuous or discrete adjustment of operating states or operating speeds, etc. Soft-elastic adhesive elements 28, which prevent the user's hand from slipping off when the electric toothbrush 12 is being used, are arranged in the actuating portion 20 on the surface which is otherwise formed by a hard material. In the embodiments of the basic body 10 which are shown in FIGS. 1-4, the actuating portion 20 tapers preferably continuously in the direction of the plug-on portion 22.

The plug-on portion 22 serves for coupling the plug-on brush 14 mechanically to the basic body 10 of the electric toothbrush 12. It comprises, in the embodiment of the basic body 10, as shown in FIG. 1, an end region of an output shaft 30 and, in the embodiment shown in FIG. 3, additionally a connection piece 32 for the rotationally fixed reception of the plug-on brush 14.

The head 38 forms a free end region, adjoining the neck 34 and generally widening with respect to the neck 34, of the plug-on brush 14. It serves for the reception or mounting of cleaning elements 40 which are equipped with bristles 42 or bundles of bristles 42 on the top side 24 in the embodiments shown in FIG. 2 and FIG. 4. Moreover, on an underside 44, not shown in FIGS. 2 and 4, which lies opposite the top side 24, the head 34 may be equipped, for example, with a tongue cleaner consisting preferably of soft material.

In the embodiment of the electric toothbrush 12 according to the invention, as shown in FIG. 2, the cleaning element 40 is arranged fixedly on the plug-on brush 14 and, in an active operating state of the electric toothbrush 12, executes, together with the entire plug-on brush 14, the reversible pivoting movement transmitted by the output shaft 30. In the embodiment of the electric toothbrush according to the invention, as shown in FIG. 4, the cleaning element 40 is mounted pivotably with respect to the head 38 and to the neck 34. In the active operating state of the electric toothbrush 12, the cleaning element executes a reversibly rotating movement about an axis which runs virtually at right angles with respect to the longitudinal axis of the neck 34. Although the resulting movement sequences of the cleaning elements 40 of the embodiments of the electric toothbrush 12 according to the invention which are shown in FIG. 2 and FIG. 4 are different from one another, both movement sequences are based on a reversible pivoting movement of the output shaft 30.

Figure 5:
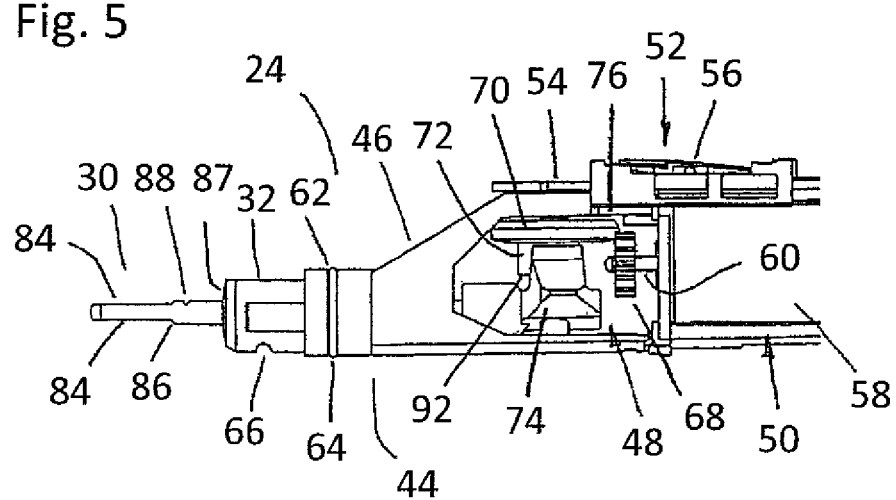
FIG. 5 shows a side view of part of the interior of the electric toothbrush according to the invention, containing, inter alia, an internal framework which is received in a basic body shown in FIGS. 3 and 4 and in which are arranged an electric motor with a drive shaft and a transmission according to the invention with the output shaft.

Inside the basic body 10 of the electric toothbrush 12 is arranged what is known as an internal framework 46. The internal framework 46 is shown in FIG. 5 in a side view of part of the interior of the electric toothbrush 12. The part illustrated extends from the outermost plug-on brush-side end of the output shaft 30 about as far as the longitudinal center of the actuating portion 20. A gear 48 according to the invention, a drive unit 50 and a control unit 52 are arranged on the internal framework 46, the two last-mentioned being only partially visible in FIG. 5.

The control unit 52 is arranged on the internal framework 46, partially on the top side, and comprises a circuit board 54 with components arranged on it and a switching element 56 for switching the active operating state of the electric toothbrush 12 on and off. The switching element 56 is designed correspondingly to the actuating elements 26 which are arranged on the basic body 10 so as to be accessible from outside. The actuating elements 26 are preferably shaped from a soft-elastic material and make it possible, when actuated, to exert actuating forces on the switching element 56.

The drive unit 50 comprises an energy store, not shown in FIG. 5, in the form of one or more batteries or of an accumulator, or a mains connection which is in each case connected electrically to an electric motor 58. The electric motor 58 provides, on its assigned drive shaft 60, a continuous rotational movement in one direction of rotation through 360°.

In a state in which the electric motor is not loaded by the alternating cleaning action, its rotational speed, with the transmission 48 connected and with the plug-on brush 14 plugged on, amounts to between 1000 revolutions per minute (rev/min) to 15 000 rev/min, preferably 3000 rev/min to 8000 rev/min or 8000 rev/min to 12 000 rev/min. By motors having these high rotational speeds being used, a high cleaning action for these cleaning elements 40 moving at a correspondingly high speed is made possible. The operating voltage for feeding to the electric motor 58 is 1.3 V to 3 V, in the case of a current flux in no-load operation defined above it is between 300 mA to 1500 mA, preferably 400 mA to 1200 mA.

On the internal framework 46, the transmission 48 according to the invention adjoins the drive unit 50 on the output side. The transmission 48 transmits and converts the essentially continuous rotational movement provided by the electric motor 58 at the drive shaft 60 into a reversible movement of the output shaft 30. The movement provided on the output shaft 30 by the transmission 48 according to the invention, described in detail below, may in this case be a reversibly pivoting movement about the longitudinal center line of the output shaft 30, a reversibly translational to-and-fro movement in the direction of the output shaft 30 or a combined movement consisting of reversibly pivoting and reversibly translational movement components.

To seal off the components 48, 50, 52, 54, 56, 58 arranged on the internal framework 46 against the penetration of liquids and solids into the basic body 10, a sealing groove 62 is shaped out on the internal framework 46 on the output-shaft side, a sealing O-ring 64 or a lip seal being inserted into said sealing groove. The connection piece 32, likewise shaped out on the internal framework 46, is manufactured, in the same way as the entire internal framework 46, from a stable hard material and has a plug-on brush notch 66 on the underside. This plug-on brush notch 66 cooperates with an element, described later, on the plug-on brush 14 and prevents an undesirable removal of the plug-on brush 14 from the basic body 10. Moreover, the connection piece 32 is equipped with edges running essentially parallel to the output shaft 30, in order, as already mentioned, to ensure a rotationally fixed arrangement of the plug-on brush 14 on the basic body 10.

To mount the output shaft 30 on the internal framework 46, the internal framework 46 is equipped on the output-shaft side with a corresponding shaft recess, not shown in the figures. The diameter of the shaft recess is in this case selected such that the output shaft 30 can move in the latter freely in translational and/or rotational movement, but the penetration of liquids and solids is as far as possible ruled out.

Figure 6:
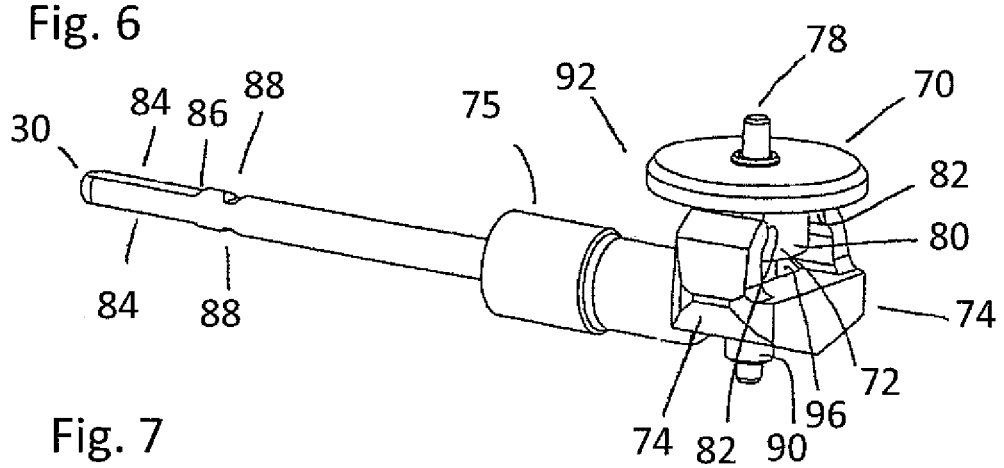
FIG. 6 shows a perspective view of a step-up stage of the transmission according to the invention with a contrate wheel, on which is arranged a cam which is sensed by a bracket-shaped pick-up connected fixedly to the output shaft.
Figure 7:
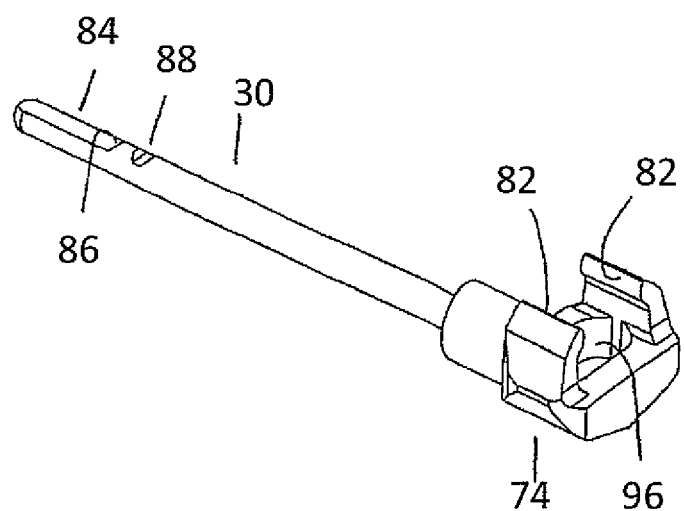
FIG. 7 shows a perspective illustration of the pick-up shown in FIG. 5 and FIG. 6.

The transmission 48 comprises, in addition to the drive gearwheel 68, shown in FIG. 5, which is arranged fixedly in terms of rotation on the drive shaft 60 of the electric motor 58, a contrate wheel 70, which, in particular, can be seen clearly in FIG. 6, with a cam 72 arranged on its toothed side face and a pick-up 74, shown particularly in FIG. 7, which is in interaction with the cam 72. The output shaft 30 is arranged fixedly in terms of rotation on the pick-up 74. The output shaft 30, in turn, is mounted rotatably and, if appropriate, also displaceably in an output shaft sleeve 75 which can be seen in FIG. 6. By the output shaft sleeve 75 being fastened to the internal framework 46, the position of the pick-up 74 with respect to the internal framework 46 is fixed with the exception of the desired degree of freedom of pivoting and, if appropriate, of displacement. The output shaft sleeve 75 thus serves for mounting the output shaft 30.

The spur-toothed drive gearwheel 68 is in engagement with teeth, not depicted for the sake of simplicity, of the contrate wheel 70 and forms a step-down 76 on account of the smaller number of teeth of the drive gearwheel 68 than that of the contrate wheel 70. The step-down 76 is a first transmission stage of the transmission 48 in the form of a contrate gear. The step-down ratio is 0.2 to 0.9, preferably 0.4 to 0.6, that is to say the rotational speed of the contrate wheel 70 is reduced by the amount of said step-down ratio with respect to the motor rotational speed and the torque is increased correspondingly. In this case, the drive shaft 60 of the drive gearwheel 68 is at least virtually at right angles to the contrate wheel shaft 78 mounted in the internal framework 46 (see FIG. 6). It is, of course, also possible to implement other step-down ratios or step-down systems and in any event design further transmission stages as step-downs 76.

In the embodiment illustrated in FIG. 5, the drive shaft 60 is positioned parallel, but not coaxially, to the output shaft 30. In order to arrange the plug-on brush 14 at an inclination with respect to the basic body 14, the drive shaft 60 and the output shaft 30 must also form the same angle. For ergonomic reasons, an angle smaller than 20°, preferably of between 3° and 10°, is preferred. In this design variant shown in FIGS. 53 to 56, the internal framework 46 is modified with respect to the variant illustrated in FIG. 5, so that the output shaft 30, the output shaft sleeve 75 and the pick-up 74 are at said angle to the drive shaft 60. In this case, as also in the embodiment shown in FIG. 6, the drive shaft 60 of the drive gearwheel 68 is likewise oriented virtually at right angles to the contrate wheel shaft 78 mounted in the internal framework 46.

Should there alternatively be a need for orienting the drive shaft 60 coaxially with respect to the output shaft 30, the cam 72 may be produced as a component separate from the contrate wheel 70. The drive shaft 60 and the output shaft 30 can thereby be positioned in the same alignment by means of a corresponding mounting. For this purpose, the pick-up 74 must be arranged so as to be rotated, for example, through 180° about its longitudinal axis and be provided with a corresponding recess, through which the cam 72 arranged fixedly in terms of rotation on the contrate wheel 70 engages with sufficient play.

The cam 72 is integrally formed fixedly on the toothed side face of the contrate wheel 70 or may be connected fixedly as an additional part to the contrate wheel 70. Consequently, a complete revolution of the contrate wheel 70 through 360° also leads to a complete rotation of the cam 72. The cam 72 may be designed differently in shape and arrangement with respect to the contrate wheel shaft 70, as shown by way of example in FIGS. 8 to 11. The cam 72, in its various embodiments, has in each case at least one curved wall 80 which extends essentially parallel to the contrate wheel shaft 78 and at right angles to the toothed side face of the contrate wheel 70.

As shown in FIG. 6, the pick-up 74 surrounds the cam 72 in a bracket-like manner and senses the curved wall 80 of the cam 72 in a sliding manner by means of two rounded sensing edges 82 lying parallel and opposite one another at a fixed distance. On account of the fixed distance between the sensing edges 82 and the cross section, deviating from a circular shape, of the cam 72 or, if appropriate, its eccentric arrangement with respect to the contrate wheel shaft 78, the pick-up 74, together with the output shaft 30 connected fixedly in terms of rotation, are pivoted reversibly about their longitudinal center line within an angular range smaller than 360°. On account of the pivoting movement of the pick-up 74 and the consequently different distance of the sensing edges 82 from the contrate wheel 70, it may be advantageous to configure the cam 72 in the direction of the contrate wheel shaft 78 so as to be slightly crowned or cask-shaped. As a result, the pivoting movement of the pick-up 74 and a reduction in the distance, projected on to a plane parallel to the toothed side face of the contrate wheel 70, between the sensing edges 82 are compensated. In the case of a pivoting movement with low deflections, this fact may be ignored.

The ratio of the distance between the longitudinal mid-axis of the output shaft 30 and the longitudinal mid-axis of the drive shaft 60 in the region of the pick-up 74 to the distance between the longitudinal mid-axis of the contrate wheel shaft 78 driving the cam 72 and the longitudinal mid-axis of the cam 72 arranged on the contrate wheel 70 (that is to say, the eccentricity of the cam 72) amounts to at least 10:1.

Since the cleaning element 40 either is arranged fixedly on the plug-on brush 14 and the plug-on brush 14 is plugged fixedly in terms of rotation directly onto the output shaft 30, as in the embodiment of the electric toothbrush 12, as shown in FIG. 2, or else is connected indirectly to the output shaft 30 via a plug-on shaft having a deflection element, as in the embodiment of the electric toothbrush 12, as shown in FIG. 4, the reversible pivoting movement of the output shaft 30 is transmitted to the cleaning element 40.

The output shaft 30 itself has a virtually constant diameter over its entire length, which diameter amounts to between 2 mm and 6 mm, preferably to between 2.5 mm and 4 mm. On the plug-on brush side, the output shaft 30 is provided in its end region with flattenings 84 on both sides. The flattenings 84 have the task of transmitting a torque in cooperation with corresponding counterfaces of the plug-on brush 14 or of the plug-on shaft. It is, of course, also possible to equip the output shaft 30 with only one flattening 84. The remaining cross section of the output shaft 30 amounts in the region of the flattenings 84 to 0.5 mm to 3.5 mm, preferably 1.5 mm to 2.5 mm. The length of the flattenings 84 along the output shaft 30 amounts to between 8 mm and 14 mm, preferably between 10 mm and 12 mm.

At the transition from the flattened cross section of the output shaft 30 to its full circular cross section, virtually planar shoulders 86 are shaped out. The shoulders form an angle with the longitudinal center line of the output shaft 30 of 30° to 60°, preferably 40° to 50°. The start of the shoulders 86 is positioned with a measurement of about 15 mm to 22 mm, preferably of 17.5 mm to 19.5 min, from a plug-on portion-side end face 87 of the basic body 10 (without the connection piece 32).

The flattenings 84 are followed on the output shaft 30 in the direction of the pick-up 74 by one, as shown in FIG. 5, or two, as shown in FIG. 6, notches 88 which are arranged opposite one another. The notches 88 give the plug-on brush 14 or the plug-on shaft a hold in the axial direction and thus prevent an undesirable removal or uncontrolled fall of the plug-on brush 14.

The notches 88 are arranged at a distance of about 12 mm to 20 mm, preferably 15 mm to 17 mm, away from the end face 87. They preferably have a depth of 0.2 mm to 0.8 mm, preferably of 0.35 mm to 0.65 mm. A bottom of the notches 88 has approximately a width of 0.3 mm to 1.5 mm, preferably of 0.7 mm to 1.1 mm.

The output shaft 30 is rounded in its end region on the plug-on brush side, in order to reduce the risk of injury and to make the mounting operation easier when the plug-on brush 14 is being plugged on.

The output shaft 30 is preferably manufactured from a metal, for example stainless steel, and has a free length, measured from the end face 87, of 25 mm to 35 mm, preferably of 28 mm to 32 mm.

In all plug-on brushes 14 in which the neck 34 is co-moved, a free distance is present between the end face 87 and the neck-side end of the plug-on brush 14, in order to avoid contact and therefore frictional losses between the plug-on brush 14 and the basic body 10. This distance amounts to between 0.2 mm and 0.8 mm, preferably to between 0.4 mm and 0.6 mm.

Various embodiments of contrate wheels 70 with cams 72 arranged on them, then, are described below with reference to FIGS. 8-11. In these figures too, the teeth of the contrate wheels 70 are not depicted for the sake of simplicity and are illustrated merely symbolically by a ring. In each case cylindrical contrate shaft sleeves 90 are shaped out, opposite the toothed side face of the contrate wheel 70, on the cams 72. Said contrate shaft sleeves serve for supporting the contrate wheel 70 along the contrate wheel shaft 78 with respect to the internal framework 46.

Figure 8:
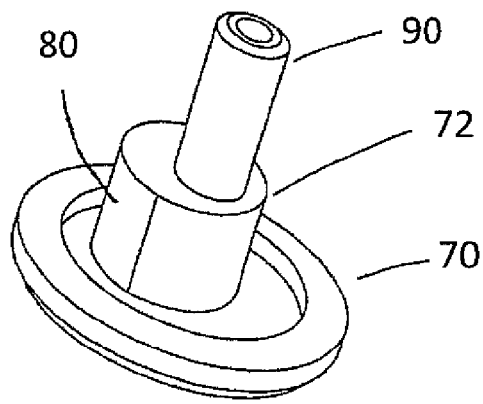
FIG. 8 shows a perspective illustration of the contrate wheel with a cam of known geometry and arrangement.

FIG. 8 shows an embodiment of a cam 72. This cam 72 has a circular to slightly elliptic cross section (with a ratio of main vertex to secondary vertex of 1.01:1 to 1.1:1, preferably 1.03:1 to 1.07:1) and is arranged eccentrically with respect to the contrate wheel sleeve 90 and to the contrate wheel shaft 78, not depicted. The distance from the contrate wheel shaft 78, which has the function of an axis of rotation for the contrate wheel 70, to a mid-axis of the cam 72 is 0.5 mm to 3.0 mm, preferably 1.5 mm to 2.5 mm.

Figure 9:
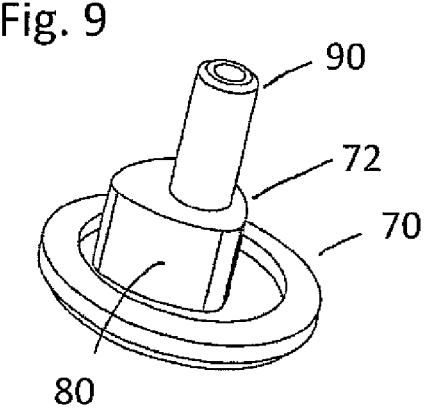
FIG. 9 shows a perspective view of part of an embodiment of the transmission according to the invention with the contrate wheel, on the toothed side face of which a triangularly rounded cam is arranged eccentrically with respect to the axis of rotation of the contrate wheel.
Figure 10:
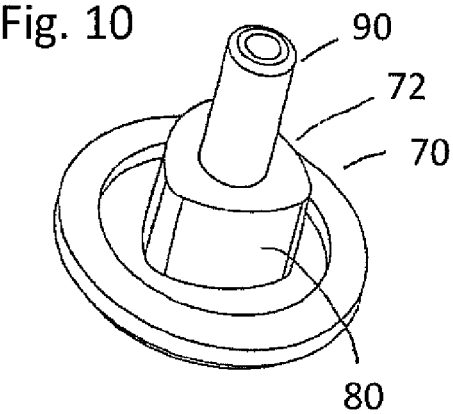
FIG. 10 shows a perspective illustration of part of a further embodiment of the transmission according to the invention with a triangular cam which is arranged concentrically with respect to the axis of rotation of its assigned contrate wheel.
Figure 11:
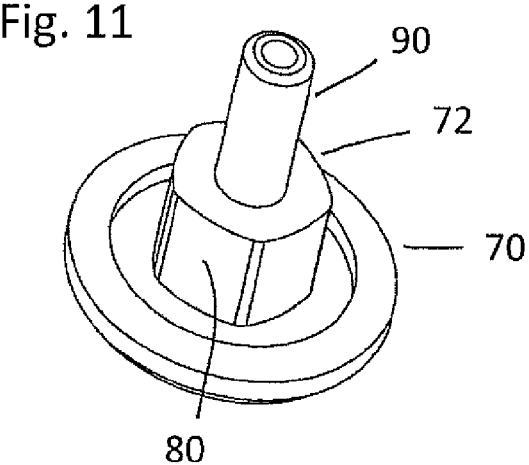
FIG. 11 shows a perspective illustration of part of a further embodiment of the transmission according to the invention with a pentagonally rounded cam mounted concentrically with respect to the axis of rotation of its assigned contrate wheel.

FIGS. 9 to 11 illustrate embodiments according to the invention of the cam 72. The cross sections of the cams 72 in each case have the form of a polygon rounded on all sides and with n sides, n being an odd positive number. Thus, FIGS. 9 and 10 show cams with an essentially triangular cross section, and FIG. 11 shows a cam with an essentially pentagonal cross section.

The curved walls 80 of the cams 72 are in this case always rounded and also contain the corners of the respective n-sided polygonal shape in order to allow sliding sensing by the sensing edges 82 of the pick-up 74. The rounding radius for the corners amounts to 1.32 mm in the case of the triangular cross section and to 0.5 mm in the case of the pentagonal cross section. The radius of the rounding of the sides amounts to 7.27 mm in the case of the triangular cross section and to 14.44 mm in the case of the pentagonal cross section. What is generally true is that the rounding radius for the corners decreases with an increasing number n, that is to say approaches 0 mm, and that the radius for rounding of the sides increases with an increasing number n.

On account of the fixed distance of the sensing edges 82 from one another, the cross-sectional shapes of the cams 72 must be configured correspondingly and, in particular, possess a circumcircle. The cross sections of the cams are preferably designed as rounded regular n-sided polygons. The curved walls 80 of the cams 72 are in this case each shaped in such a way that each cross-sectional length limited by the curved walls 80 and running in a cross-sectional plane of the cam 72 through the center point of its cross-sectional shape possesses approximately equal length.

The cams 72 essentially in the form of an n-sided polygon may be arranged both eccentrically with respect to the contrate wheel shaft 78 and, as shown in FIGS. 10 and 11, concentrically with respect to the contrate wheel shaft 78. For n-sided cross-sectional shapes of the cams 72, in the case of one complete revolution of the contrate wheel 70 through 360°, an n-fold reversible pivoting of the pick-up 78 and of the output shaft 30 connected to it is obtained.

In the case of an eccentric arrangement of an n-sided cam 72, additional n "smaller" pivotings are superposed on a "large" reversible pivoting of the pick-up. On account of the eccentric arrangement of the cam 72, for example, a plurality of "smaller" pivoting movements may be superposed on a dominant basic pivoting having a "large" pivoting range. In this case, the output shaft 30 pivots exactly once per revolution of the contrate wheel 70 on account of the eccentric arrangement of the cam 72 and n times on account of the n-sided configuration of the cam 72. This arrangement is described in detail below in connection with FIG. 19.

For n>1, that is to say for cams 72 with 3, 5, 7 etc. —sided cross-sectional shapes, the combination of the cam 72 with the pick-up 74 forms an output-side second transmission stage in the form of a gearwheel-free step-up 92 (see, for example, FIG. 6). The corresponding step-up ratios 3, 5, 7 etc. cause an increase in the pivoting frequency of the pick-up 74 with respect to the rotational speed of the contrate wheel 70 by the amount of these very step-up ratios mentioned. The deflection of the pick-up 74 gives rise overall (or totally), depending on the specific cross-sectional shape of the cam 72, to a maximum deflection of the pick-up 74 or of the output shaft 30 connected to it of between 1° and 23°, preferably of between 3° and 15°, particularly preferably of about 5° to 12°, between its maximum deflection positions (that is to say, the full deflection angle in the case of a movement from the far left on the outside to the far right on the outside). It is, of course, also possible to set further step-up ratios or to precede or follow with further step-ups 92 or step-downs 76 or run these in parallel.

The second transmission stage is preferably accommodated in the basic body 10 of the electric toothbrush 12. However, it would, of course, also be conceivable to arrange at least one of the two transmission stages in the plug-on brush 14. This special embodiment by means of the cam 72 and pick-up 74 is, of course, merely exemplary, and other means, not shown here, may be used in order to implement the at least second step-up transmission stage. Preferably, however, this second transmission stage is not implemented by means of a toothing, but, instead, by means of curves or cams and correspondingly shaped pick-ups.

Figure 12:
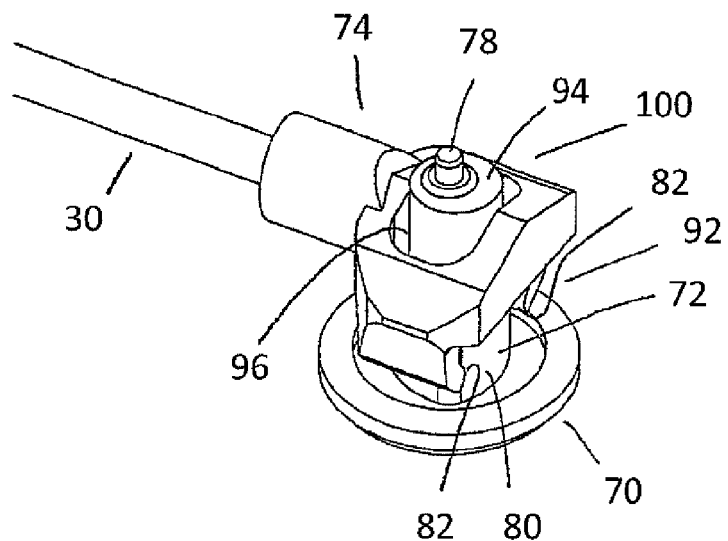
FIG. 12 shows a perspective illustration of a further embodiment of the step-up stage of the transmission according to the invention with a contrate wheel, on the toothed side face of which are arranged a cam and, above the cam, a cam prolongation, which are both sensed by the pick-up.

The reversible pivoting movements brought about in each case by means of the specific designs of cams 72 on the output shaft 30 are described in detail below in connection with FIGS. 16 to 19. FIG. 12 shows, in a similar way to the illustration in FIG. 6, a structural unit consisting of the contrate wheel, of the cam 72, of the pick-up 74 and of the output shaft 30 connected to it. In contrast to the embodiments described hitherto, however, in this case the contrate shaft sleeve 90 shown in FIGS. 8 to 11 is replaced by a cam prolongation 94. This cam prolongation 94 passes through a sensing recess 96 in the pick-up 74. The sensing recess 96 has a rounded cross section which is delimited by a sensing wall 98 and within which the cam prolongation 94 can execute as low-friction a rotational movement as possible about the contrate wheel shaft 78, and a pivoting movement of the pick-up 74 about the output shaft 30 is made possible at the same time.

Figure 13:
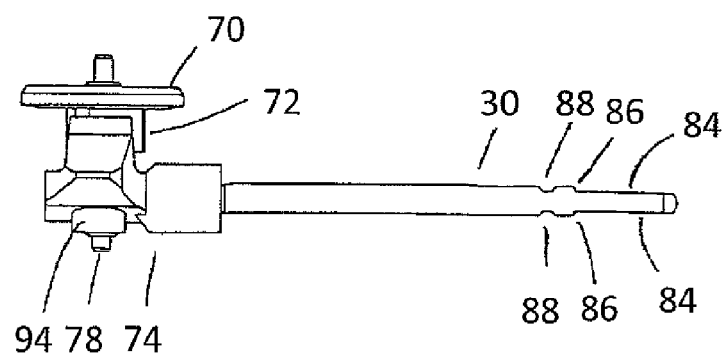
FIG. 13 shows a side view of the step-up stage shown in FIG. 12.

In the embodiment shown in FIG. 12 and FIG. 13, the cam prolongation 94 has a circular to slightly elliptic cross section (with a ratio of the main vertex to the secondary vertex of 1.01:1 to 1.08:1, preferably 1.02:1 to 1.05:1) and is arranged eccentrically with respect to the contrate wheel shaft 78. The distance from the contrate wheel shaft 78, which performs the function of an axis of rotation, to a mid-axis of the cam prolongation 94 amounts to between 0.1 mm to 1.5 mm, preferably 0.2 mm to 0.8 mm. Consequently, during a revolution of the contrate wheel 70, the pick-up 74 is not only pivoted about the output shaft 30, but, because of the engagement of the cam prolongation 94 into the sensing recess 96, is at the same time also moved reversibly to and fro in translation in the direction of the output shaft 30. An exact description of the form of movement is given in connection with FIG. 20.

FIG. 13 illustrates once again a side view of the arrangement shown in FIG. 12, and in this, particularly, the passage of the cam prolongation 94 through the sensing recess 96 can be seen clearly. The contrate wheel 70 used in this arrangement, with a concentrically arranged, essentially triangularly rounded cam 72 and with a cam prolongation 94 which is placed above the cam 72 and which has an essentially oval cross section and is arranged eccentrically with respect to the contrate wheel shaft 78, is once again shown, set apart and enlarged, in FIG. 14.

All the features mentioned hitherto with regard to the cam 72 in terms of its cross-sectional shape and the arrangement in relation to the contrate wheel shaft 78 may also be transferred to the cam prolongation 94. This means, in concrete terms, that the cam prolongation 94, too, may be equipped with a rounded, essentially n-sided cross section, n being an odd positive number, and the formation of a gearwheel-free further step-up 100 being effected for n>1. In particular, in this case, the cam prolongation 94 may be arranged both eccentrically and concentrically or coaxially with respect to the contrate wheel shaft 78. Moreover, the cam prolongation 94 is shaped in such a way that each cross-sectional length limited on two sides by its outer wall and running in a cross-sectional plane of the cam prolongation 94 through the center point of its cross-sectional shape is at least virtually of equal length.

Figure 15:
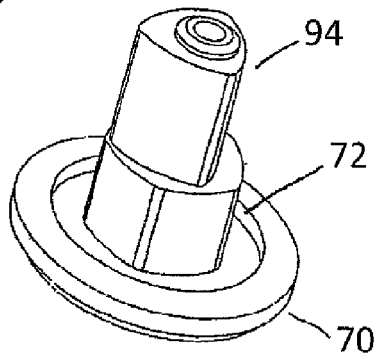
FIG. 15 shows a perspective illustration of a further embodiment of the contrate wheel with a pentagonally rounded cam and with a triangularly rounded cam prolongation mounted eccentrically with respect to the axis of rotation of the contrate wheel.

One example of a cam prolongation 94 with a triangularly rounded cross section, said cam prolongation being arranged eccentrically with respect to the contrate wheel shaft 78, is shown in FIG. 15. Here, the cam prolongation 94 is combined with a pentagonally rounded cam 72 on the contrate wheel 70. The cam 72 is arranged here concentrically or coaxially with respect to the contrate wheel shaft 78. A movement pattern thereby capable of being generated on the output shaft 30 is explained below in connection with FIG. 20.

Figure 14:
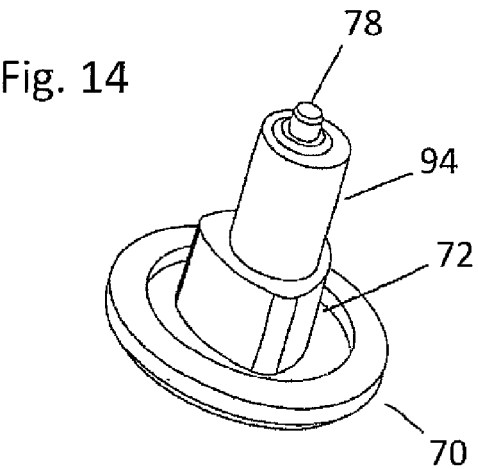
FIG. 14 shows a perspective illustration of the contrate wheel shown in FIG. 12 and FIG. 13, with a triangularly rounded cam and with a cam prolongation which is arranged above the cam, eccentrically with respect to the axis of rotation of the contrate wheel and which has a circular cross section and is arranged eccentrically with respect to the axis of rotation of the contrate wheel.

It may be mentioned at this juncture that it is, of course, also possible to shape the embodiments of cams 72 shown in FIGS. 14 and 15 cylindrically and to arrange them concentrically with respect to the contrate wheel 70. In this case, the output shaft 30 is merely reversibly moved to and fro in translation and is not additionally reversibly pivoted. The cylindrically shaped, concentrically arranged cam 72 stabilizes the pick-up 74 laterally and prevents the pivoting movement. In the opposite case, if only a reversible pivoting movement is implemented, the cam prolongation 94 is shaped cylindrically and concentrically and stabilizes the pick-up 74 in the direction of the output shaft 30 and prevents the translational movement.

The reversible translational to-and-fro movement caused by the rotation of the cam prolongation 94 gives rise on the output shaft 30 to a displacement in its longitudinal direction of between 0.5 mm and 2 mm, preferably of between 0.5 mm and 1.5 mm. A reversibly translational movement component of the cleaning element 40 can be implemented, for example, in the embodiment of an electric toothbrush 12 according to the invention, as shown in FIG. 2. In this case, however, care must be taken to ensure that, in this instance, suitable safety measures must be taken, so that no body parts or skin regions of the user can be pinched by the plug-on brush 14 lifting off from the basic body 10. Such a safety measure is, for example, the insertion of a concertina-like hose between the end region of the plug-on portion 22 of the basic body 10 and the free end region of the neck 34 of the plug-on brush 14 or similar means consisting of soft-elastic material which keep the gap occurring as a result of the translational movement of the plug-on brush 14 to a minimum. Another safety measure is to cause the plug-on brush 14 to end within the basic body 10 and thus prevent the risk of pinching.

With reference to FIGS. 16 to 20, then, the movement patterns which can be achieved by means of the units shown in each case on the left side and consisting of the contrate wheel 70, of the cam 72, of the contrate shaft sleeve 90 or of the cam prolongation 94 can be explained. In the graphic illustrations of FIGS. 16 to 19, the ordinate in each case represents a deflection angle φ during the pivoting of the output shaft 30. In the case of a reversibly translational movement of the output shaft 30, which may take place, for example, as a result of an interchange in position of the cam 72 shown in each case with the assigned contrate shaft sleeve 90, the ordinate likewise represents a deflection length s. In each case the time t or the corresponding angle of rotation θ of the contrate wheel 70 (or of the drive shaft 60) is plotted on the abscissa. The deflection angle φ is in each case illustrated for one complete revolution (angle of rotation θ=0 . . . 2π or 0 . . . 360° of the contrate wheel 70.

When a cam 72 of oval cross section, which is mounted eccentrically with respect to the contrate wheel shaft 78, is used, a sinusoidal function of the deflection angle φ is obtained during the rotation of the contrate wheel 70 (FIG. 16). In this special instance, no step-up 92 by the second transmission stage is implemented, but, instead, only a deflection into a reversible pivoting movement of the output shaft 30. The exact starting point of the curve depends on the position of the contrate wheel 70 in relation to the pick-up 74, but the curve shape per se remains the same.

When a cam 72 with an essentially triangularly rounded cross section and centric arrangement with respect to the contrate wheel shaft 78 is used; a step-up ratio of 3 is obtained, this being expressed in the graphic illustration of FIG. 17 by a sinusoidal function with three deflection periods within one revolution of the contrate wheel 70. If the cam 72 were additionally arranged eccentrically with respect to the contrate wheel shaft 78, these three successive oscillation periods would additionally be modified by a sinusoidal deflection with a period within the rotation of the contrate wheel 70, as shown, for example, in FIG. 16. The phase relation between the two sinusoidal components depends in this case on the exact position of the corners of the cam 72 with respect to the contrate wheel shaft 78 (see also FIG. 19).

In the graphic illustration of FIG. 18, the deflection angle φ of the output shaft 30 is shown as a function of the angle of rotation θ for the contrate wheel 70 and of the time for an essentially pentagonal cam 72 which is arranged concentrically with respect to the contrate wheel shaft 78. In this case, the deflection angle φ passes through five sinusoidal periods during one revolution of the contrate wheel 70. There is consequently a step-up ratio of 5.

FIG. 19 illustrates a movement pattern for the case, already mentioned in connection with FIG. 17, of an essentially triangular cam 72 which is mounted eccentrically with respect to the contrate wheel shaft 78. In this case, the cam 72 is displaced along an angle-bisecting line from the center point of the circumcircle of the cam cross section in the direction of one corner. This consequently gives rise to the functional dependence of the deflection angle φ on the angle of rotation θ of the contrate wheel 70 (or of the drive shaft 60) essentially on account of a superposition of the functional dependencies illustrated in FIG. 16 and FIG. 17. A function profile of this type leads to a jitter-like deflection of the output shaft 30. By a suitable choice of the number n of corners of the cam cross section and a specific position of the cam 72 with respect to the contrate wheel shaft 78, a multiplicity of deflection patterns can be generated by two sinusoidal oscillations being superposed.

FIG. 20 illustrates the movement pattern of the output shaft 30 under an additional influence of the cam prolongation 94. In this case, as in the preceding movement graphs, the deflection angle φ of the output shaft 30 is plotted on the ordinate. The abscissa in this case represents a deflection length s of the output shaft 30. In this case, too, the movement pattern for one complete revolution of the contrate wheel 70 over an angle of rotation of 2π (360°) is illustrated.

In a similar way to the illustration in FIG. 17, the reversibly pivoting movement component causes a sinusoidal variation of the deflection angle φ for three periods within one contrate wheel revolution. At the same time, the cam prolongation 94, having a cross-sectional geometry and arrangement similar to that of the cam 72 shown in FIG. 16, causes a reversibly translational to-and-fro movement along the output shaft 30. On account of the frequency ratios, in this graph, an operating point first passes through 1.5 deflection periods of the deflection angle φ during an outward movement and, mirror-symmetrically with respect to the abscissa, the remaining 1.5 periods during the return movement. Thus, in the selected illustration of FIG. 20, a closed curve having three virtually elliptical curve elements is obtained. In this case, too, a multiplicity of movement patterns can be achieved by a variation in the cross sections of the cam 72 and of the cam prolongation 94 and also the choice of various positionings of the cam 72 or of the cam prolongation 74 with respect to the contrate wheel shaft 78.

The following table lists by way of example some forms of movement as a function of the position and cross-sectional shape of the cam 72 or of the cam prolongation 74.

case, in particular, superposing movement patterns described above have proved appropriate. It has been possible, in particular, to perfect the movement patterns of what is known as the bass method, employed for manual toothbrushes, by means of the method described above.

The pivoting movement of the movable cleaning element 40 is implemented with a frequency of between 3000 rev/min and 15 000 rev/min, preferably of 8 000 rev/min to 12 000 rev/min, particularly preferably between 8000 and 10 000 rev/min. The translational to-and-fro movement of the cleaning element 40 is implemented at a frequency of between 1000 rev/min and 12 000 rev/min, preferably of between 2000 rev/min and 4000 rev/min or of between 8000 rev/min and 12 000 rev/min.

All the above-described movements of the output shaft 30 can be transmitted, in particular, to the plug-on brushes 14 in FIGS. 21-25 and 27-31. The plug-on brush 14 shown in FIG. 26 is suitable, above all, for reversibly pivoting movements of the output shaft 30, without a translational to-and-fro movement of the output shaft 30 being superposed.

It may be mentioned, with regard to all the described embodiments of transmissions 48, that the play between the

| Form of movement of the output shaft 30 | Cam 72: Cross-sectional shape, position with respect to the contrate wheel shaft 78 | Cam prolongation 94: Cross-sectional shape, position with respect to the contrate wheel shaft 78 |
|---|---|---|
| Pivoting (single) | Oval, eccentric | Oval, concentric |
| Pivoting n times | n-sided, concentric | Oval, concentric |
| Moving to and fro in translation (single) | Oval, concentric | Oval, eccentric |
| Moving to and fro in translation n times | Oval, concentric | n-sided, concentric |
| Pivoting (single) with pivoting n times superposed | n-sided, eccentric | Oval, concentric |
| Moving to and fro in translation (single) with moving to and fro in translation n times superposed | Oval, concentric | n-sided, eccentric |
| Pivoting n times with moving to and fro in translation (single) | n-sided, concentric | Oval, eccentric |
| Pivoting n times with moving to and fro in translation n times | n-sided, concentric | n-sided, concentric |
| Pivoting (single) with pivoting n times superposed and with moving to and fro in translation (single) | n-sided, eccentric | Oval, eccentric |
| Pivoting (single) with pivoting n times superposed and with moving to and fro in translation with moving to and fro in translation n times superposed | n-sided, eccentric | n-sided, eccentric |

In the above table, the note "single" means that exactly one complete pivoting period for the deflection angle φ is passed through for each complete revolution of the contrate wheel 70. As already mentioned above, the variable n is to be replaced by an odd positive number, for example 3, 5, 7, 9, etc. It is clear from the above table that a multiplicity of pivoting movements and to-and-fro movements can lead to complex movement patterns of the output shaft 30 and of the cleaning elements 40 connected to it. These can be adapted in order to bring about an optimal cleaning of the teeth and of the dental interspaces and also an improved blood flow in the gums by means of corresponding massaging movements. Intensive tests with cleaning robots have shown that high-frequency movements with relatively low deflection achieve the best cleaning values, particularly in the interdental region. In this teeth of the drive gearwheel 68 and of the contrate wheel 70 and also between the cams 72 and the sensing edges 82 and the cam prolongation 94 and the sensing walls 98 is kept as low as possible, in order to keep impacts in the system and annoying noise outside the basic body 10 as low as possible. In addition, the elements engaging one in the other or sliding one against the other may be provided with a lubricant, for example silicone grease, in order to reduce possible frictional effects. It is likewise possible to equip the components of the transmission 48, which are as a rule manufactured from a hard material, completely or at specific contact or bearing points with a damping plastic, in order to achieve as uniform and as low-noise a conversion of the movements as possible. Moreover, for example, the output shaft 30 and the drive shaft 60 may be of multipart design, the individual parts being connected to one another via coupling elements consisting of a damping plastic. By virtue of torsional movements of the shafts made possible as a result, a smooth start-up of the movements is possible and a risk of injury due to abrupt movements is reduced. Such a "smooth mounting" may also be configured without an interruption in the output shaft 30, in that, for example, the connection between the pick-up 74 and output shaft 30 has a soft configuration, that is to say a soft layer is applied between the two elements 74, 30. For a noise reduction, corresponding mountings may also be designed which damp the transmission of vibrations via the output shaft 30.

It is likewise possible, for example, to cover the sensing edges 82 or the sensing walls 98 with a soft-elastic layer or to produce the entire pick-up 74 from a somewhat softer material. Furthermore, for noise reduction, cavities or resonant spaces existing inside the basic body may be filled with sound-insulating material.

Various embodiments of plug-on brushes 14 and configurations of heads 38 and cleaning elements 40 and of the bristles 42 arranged on them are described in detail below by means of the further figures. These cleaning elements 40 are suitable, in particular, in conjunction with the movement patterns described above and reinforce their action.

Figure 21:
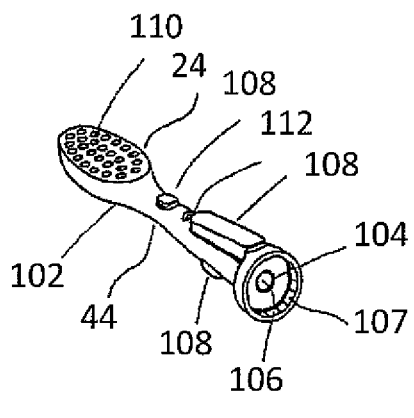
FIG. 21 shows an embodiment of a plug-on brush basic body in a perspective view showing, above all, a top side.

FIG. 21 shows a plug-on brush basic body 102, manufactured from hard material, of a plug-on brush 14 which can be plugged, for example, onto the basic body 10 shown in FIG. 1 and which can execute a reversibly pivoting movement. The plug-on brush basic body 102 is preferably produced by means of an injection molding technique. It gives the plug-on brush 14 a basic stability and serves as a backbone for the latter. An orifice 104 of a shaft receptacle 106 can be seen in the neck-side end region of the plug-on brush basic body 102, and the flattened end region of the output shaft 30 can be introduced into said orifice. The shaft receptacle 106 is equipped with two receptacle flattenings, not shown in the illustrations, which are designed correspondingly to the flattenings 84 of the output shaft 30 and, by virtue of their cooperation, ensure the transmission of a torque from the output shaft 30 to the plug-on brush 14.

It can likewise be seen in this figure that the orifice 104 is preceded on the end-region side by a cylindrical holding recess 107. The holding recess 107 serves for ensuring that the plug-on brush 14 can be plugged onto a corresponding holder for storage in a base station. The holding recess 107 occupies a substantial part of the neck cross section and has a longitudinal-side depth of less than 10 mm, preferably of less than 5 mm. The shaft receptacle 106 and the holding recess 107 are preferably arranged coaxially with respect to one another. The holding recess 107 may also perform a second function: by virtue of an appropriate configuration, a pivotable plug-on brush 14 may be formed, which can also be plugged onto the basic body 10 illustrated in FIG. 3 and FIG. 4. An outer sheath, surrounding the holding recess 107, of the plug-on brush 14 in this case surrounds the connection piece 32 in the manner of a skirt. Basic bodies 10 which can be used with plug-on brushes 14 both for oscillating and for pivoting movements are preferably equipped only with a transmission 48 for providing the pivoting movement. An additionally superposed translational movement component seems to be less expedient here.

Moreover, supporting stubs 108 consisting of hard material are shaped both on the head-side end region and in the neck-side portion on the plug-on brush basic body 102. These supporting stubs 108 serve various functions: support in an injection molding die in a subsequent injection molding method step for the injection of a soft-elastic material, and support of the plug-on brush basic body 102 during labeling, and, if appropriate, constitute, with their surface visible on the surface of the plug-on brush 14, suitable regions on which lettering can be applied, for example by means of hot pressing, inkjet or pad lettering methods.

The plug-on brush basic body 102 is already equipped on the head side with bristle reception holes 110. Furthermore, a vent hole 112 is located in each case both on the top side shown in FIG. 21 and on the underside 44 shown in FIG. 22. The vent hole 112 formed on the top side 24 and, on the shaft-receptacle side, on the underside 44 serves in the injection molding method for supporting a core for shaping the shaft receptacle 106. The top-side vent hole 112 in the plug-on brush basic body 102 is covered by soft-elastic material in the subsequent injection molding method step. The remaining underside vent hole 112 is not covered with soft-elastic material and serves for the escape of air during the introduction of the output shaft 30 and the flushing through the shaft receptacle 106 with liquid for cleaning purposes.

Figure 22:
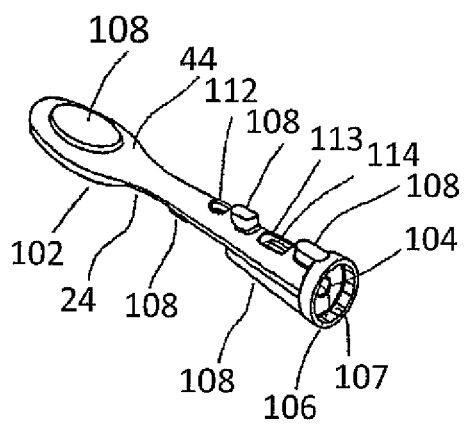
FIG. 22 shows the plug-on brush basic body shown in FIG. 21 in a perspective view showing, above all, an underside.

An essentially U-shaped recess 113 can be seen in FIG. 22 in the neck-side end region of the plug-on brush basic body 102 between the two underside supporting stubs 108. The U-shaped recess 113 surrounds a tongue-like spring element 114 having snap bosses integrally formed on it and cooperating with a notch 88 on the output shaft 30, in order to hold the plug-on brush 14 on the basic body 10 of the electric toothbrush 12.

Figure 23:
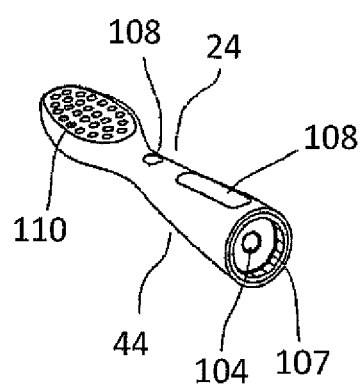
FIG. 23 shows a plug-on brush with the plug-on brush basic body shown in FIG. 21 and FIG. 22 in a perspective view showing, above all, a top side.
Figure 24:
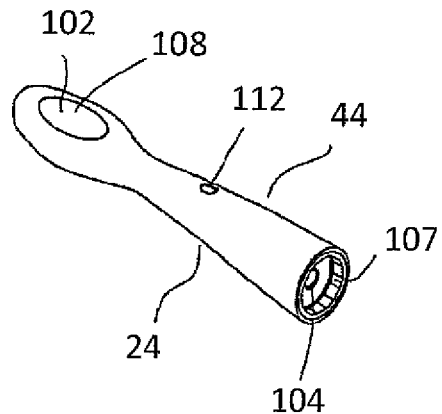
FIG. 24 shows the plug-on brush shown in FIG. 23 in a perspective view showing, above all, an underside.

FIGS. 23 and 24 show respectively the top side 24 and the underside 44 of the plug-on brush basic body 102 shown in FIG. 21 and FIG. 22, after being injection molded over with a soft-elastic material. The plug-on brush basic body 102 around which soft-elastic material has been injection-molded is subsequently equipped in the head region with bristles 42, for example by means of a conventional bristling method. The plug-on brush 14 is preferably produced from a plurality of plastic materials. Preferably, in this case, a hard and a soft material is used respectively. The various plastics adhere to one another. In the case of a combined use of hard and soft materials in the plug-on brush 14, a certain flexibility of the plug-on brush 14 can be achieved. The flexibility can be set effectively via a combination of various layer thicknesses and shapes. Furthermore, by means of the soft material, on the outer surface of the plug-on brush 14 a structure can be formed which assists the pulling off of the plug-on brush 14 from the basic body 10 in that it offers a retaining structure for the fingers of the human hand.

In order to support the head 38 during the injection molding of the soft-elastic material and during the bristling process, a supporting surface 108 is formed on the underside 44 of the brush head 38 and fixes and supports the brush head 38 during bristling.

Figure 25:
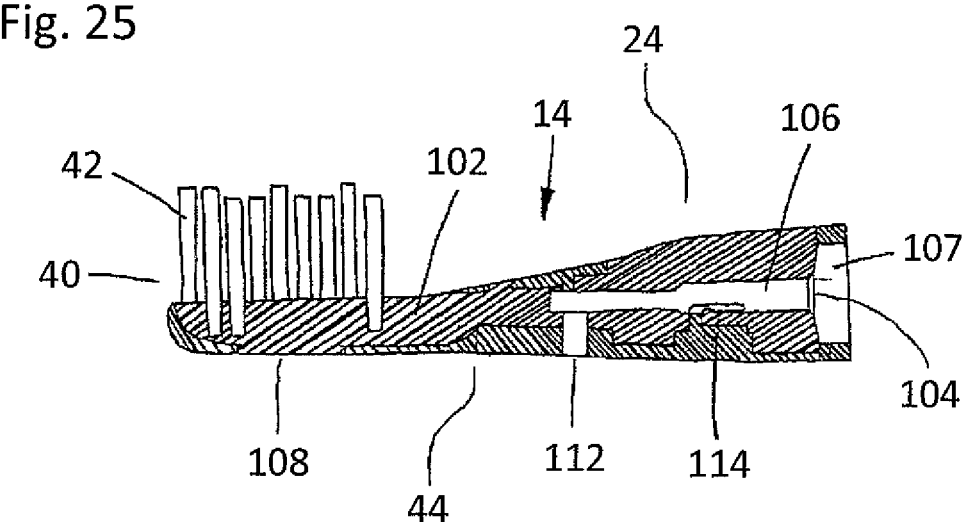
FIG. 25 shows a sectional illustration of the embodiment, shown in FIG. 23 and FIG. 24, of a plug-on brush with a bristle-fitted head.
Figure 26:
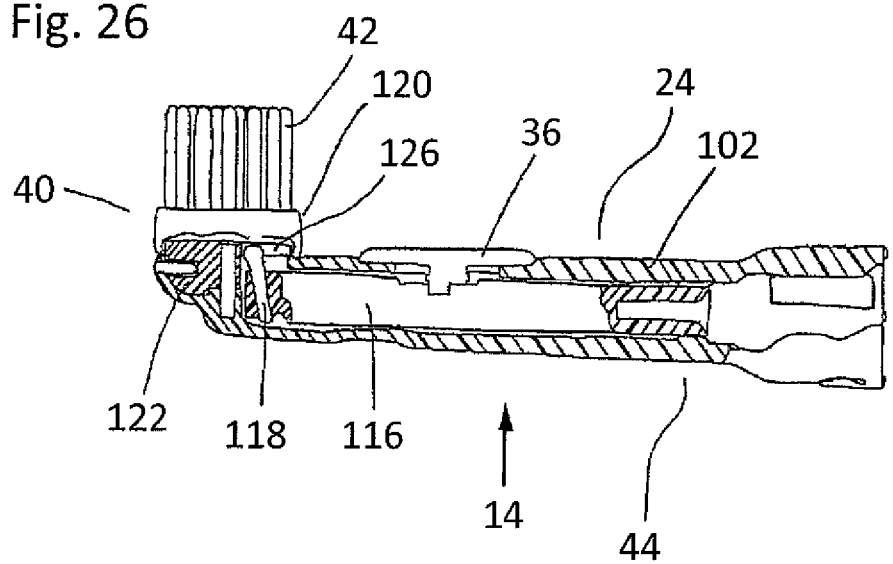
FIG. 26 shows a sectional illustration of a further embodiment of a plug-on brush with a reversibly oscillatable cleaning element, already shown in FIG. 4.

The finished plug-on brush 14 is shown in a sectional illustration in FIG. 25. In this sectional illustration, the hard material used for producing the plug-on brush basic body 102 is illustrated by a different hatching from that of the soft-elastic material injection-molded on in a second method step. The shaft receptacle 106 and the vent hole 112, not covered, can also be seen particularly clearly in this illustration.

What can likewise be seen clearly in FIG. 25 is the spring element 114 which is shaped on one side on the plug-on brush 14 and therefore makes it possible for the plug-on brush 14 to be plugged in two different orientations about its longitudinal axis onto the basic body 10. The spring element 114 is partially surrounded by soft-elastic material. By a variation in the thickness of the hard material of the spring element 114, in the extent of the snap boss and in a variation of the thickness of the surrounding soft-elastic material, a pull-off weight for pulling off the plug-on brush 14 from the output shaft 30 can be set exactly. The pull-off weight amounts to between 2 kg and 5 kg, preferably between 3.5 kg and 4.5 kg. The spring element 114 must, on account of its spring-elastic properties, move resiliently, as early as in the first injection molding method step, during the removal of the core which serves for forming the shaft receptacle 106. he same version of the spring element 114 may also be employed in an oscillating brush, as illustrated in FIG. 26.

On the underside 44, the plug-on brush shown in FIG. 25 may be additionally equipped on the head 38 with an elastomeric cleaning structure, not shown, in the form of a tongue cleaner. For this purpose, scraper edges are formed preferably from the soft-elastic material and can remove plaque and impurities from the tongue during movement. Identical soft-elastic material may be used in order to form in the bristle field soft-elastic massage elements, preferably elastomeric cleaning lamellae or cleaning structures. The scraper edges consisting of soft-elastic material preferably stand transversely with respect to the stipulated direction of movement of the brush head. If, for example, the brush head executes a reversible pivoting movement, the scraper edges are oriented preferably essentially in the longitudinal direction of the plug-on brush 14. If, for example, the brush head executes a translational to-and-fro movement in the axial direction, the scraper edges are oriented preferably essentially in the transverse direction with respect to the longitudinal axis, that is to say essentially at right angles to the longitudinal axis of the plug-on brush 14. The cleaning structures may also be formed from hard metal, in which case, of course, they are not elastomeric.

FIG. 26 is a sectional illustration of the embodiment of a plug-on brush 14, as already shown in FIG. 4. This embodiment of the plug-on brush 14 makes it possible to have a reversibly rotating or reversibly oscillating movement of the cleaning element 40. In this illustration, in particular, the plug-on shaft 116 capable of being plugged onto the output shaft 30 and having the deflection element 118 can be seen clearly. The actuating element 36, the position of which determines the relative positioning of the plug-on shaft 116 within the neck 34 and consequently determines the pivot angle range of the cleaning element 40, can likewise be seen. In this embodiment, the cleaning element 40 has a disk-shaped bristle carrier 120 and has been equipped with bristles 42 during production by a conventional bristling method by means of metal anchors, an AFT (Anchor Free Tufting) or an IMT (In Mold Tufting) method.

The bristle carrier 120 is fastened on a rotary disk 122 which is mounted pivotably on the plug-on brush basic body 102 via a rotary disk shaft 124 fastened centrically in the rotary disk 122. The rotary disk shaft 124 extends essentially at right angles to the longitudinal extent of the plug-on shaft 116 or of the output shaft 30. The rotary disk 122 has a slot 126 into which the deflection element 118 engages. By the position of the plug-on shaft 116 within the neck 34 being varied, which, as already mentioned, may take place by the actuating element 36, the radial engagement position of the deflection element in the rotary disk 122 is influenced, so that a selection can be made between a larger and a smaller pivot angle of the rotary disk 122 and consequently the cleaning element 40.

The pivot angle in this case amounts to less than 35°, preferably less than 30°. Further information on the internal set-up of this embodiment of a plug-on brush 14 may be gathered, for example, from CH 688537.

Figure 27:
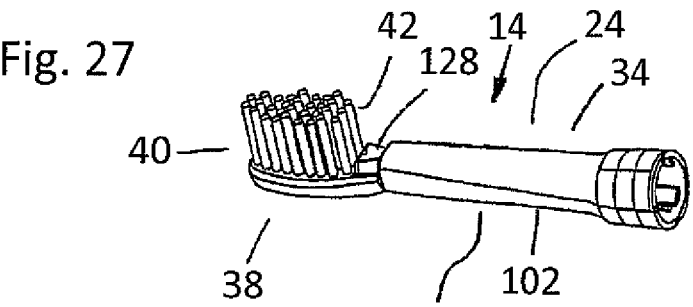
FIG. 27 shows, in a perspective view showing, above all, a top side, a further embodiment of a plug-on brush in which the cleaning element is arranged on a plug-on shaft movable inside the neck.
Figure 28:
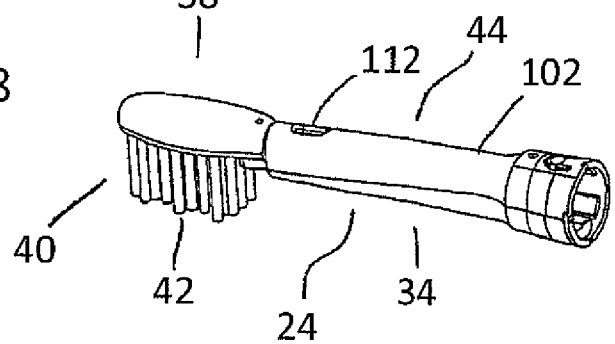
FIG. 28 shows the plug-on brush shown in FIG. 27 in a perspective view showing, above all, an underside.

A further embodiment of a plug-on brush 14 with a pivotable cleaning element 40 is illustrated in FIGS. 27 and 28. In contrast to the embodiment shown in FIGS. 2 and 21 to 25, in which the entire plug-on brush 14, together with the cleaning element 40, is pivoted, the plug-on brush basic body 102 is plugged on fixedly with respect to the basic body 10 and is not pivotable, in a similar way to the embodiment shown in FIG. 26. The cleaning element 40 is connected fixedly to a shaft prolongation 128. The shaft prolongation 128, in turn, is mounted pivotably in the plug-on brush basic body 102. When this plug-on brush 14 is being plugged onto the basic body 10, the shaft prolongation 128 is connected to the output shaft 30 in a similar way to the plug-on shaft 116 (see FIG. 26). On account of flattenings 84 which cooperate with corresponding reception sides of the shaft prolongation 128, a torque is transmitted from the output shaft 30 to the shaft prolongation 128. As seen from outside, only the movable cleaning element 40 moves. In an alternative variant, the cleaning element 40 may also be arranged at an angle or at an inclination with respect to the plug-on shaft 116. For ergonomic reasons, the angle of inclination is preferably smaller than 30°, particularly preferably smaller than 15°. Consequently, depending on the radial distance of the bristles 42 of the movable cleaning element 40 from the plug-on shaft 116, travel distances of different length can be covered by the free ends of the bristles 42.

Figure 29:
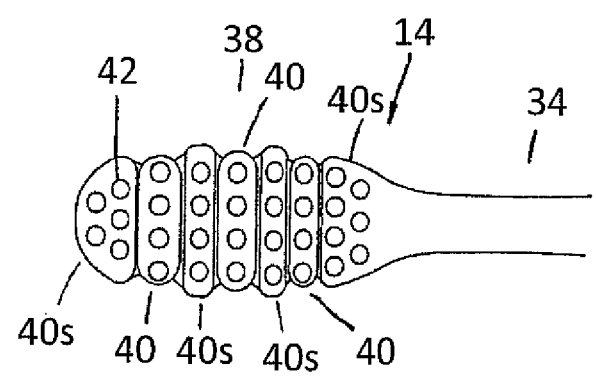
FIG. 29 shows a top view of the head of a plug-on brush with cleaning elements which are movable with respect to the neck and are stationary.
Figure 30:
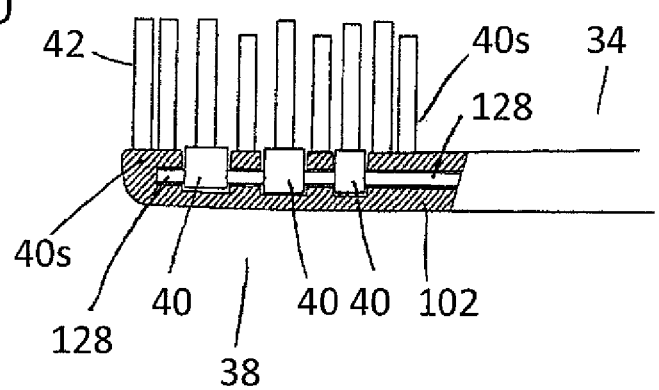
FIG. 30 shows a partially sectional illustration of the head, shown in FIG. 29, of the plug-on brush.
Figure 35:
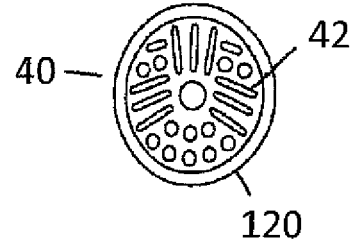
FIG. 35-FIG. 38 show top views of various embodiments of reversibly oscillatable cleaning elements with different arrangements of bristle bundles.
Figure 36:
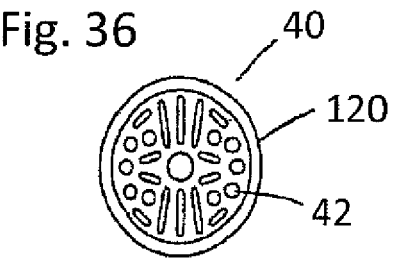
Figure 37:
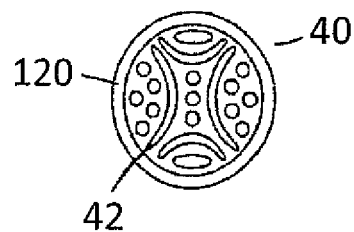
Figure 38:
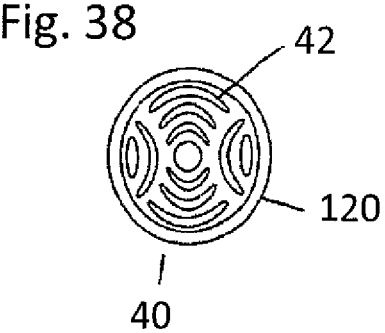

FIGS. 29 and 30 illustrate a further development of the embodiment of a plug-on brush 14, as shown in FIGS. 27 and 28. In this case, stationary cleaning elements 40s and pivotably movable cleaning elements 40 are arranged alternately along the longitudinal extent of the plug-on brush 14. As can be seen in FIG. 30, the movable cleaning elements 40 are connected fixedly in terms of rotation to the shaft prolongation 128. With the plug-on brush 14 plugged onto the basic body 10 and in the activated operating state of the electric toothbrush 12, the movable cleaning elements 40 pivot outward in relation to the stationary cleaning elements 40s, so that the bristles 42 fastened in each case to them likewise execute relative pivoting movements with respect to one another. A particularly preferred cleaning effect is thus achieved. It must be remembered that, when the plug-on shaft 116 or the shaft prolongation 128 has to be led through beneath the bristle field, the head 38 must have a greatly thickened design, so as nevertheless to achieve the required stability. If there is a sufficient distance between the stationary and the movable cleaning elements 40s and 40, the reversible pivoting movement may additionally have a translational to-and-fro movement superposed on it, as already described.

A further embodiment of a plug-on brush 14 is illustrated in FIGS. 31 and 32. In this embodiment, too, a pivotable cleaning element 40, which is arranged on the plug-on brush 14 on the end region side, can be pivoted with respect to a stationary cleaning element 40s positioned on the neck side. The pivotally movable cleaning element 40, in turn, is connected fixedly in terms of rotation to the shaft prolongation 128 and, in the active operating state of the electric toothbrush 12, is deflected with respect to the neck 34 and to the stationary cleaning element 40s on account of mechanical coupling to the output shaft 30. Moreover, this embodiment of a plug-on brush 14 is also suitable for use in the case of a combined movement having a reversibly pivoting and a reversibly translational movement component. In this case, the reversibly translational movement component causes a to-and-fro movement of the pivotally movable cleaning element 40 along the longitudinal extent of the output shaft 30. For this purpose, the transmission 48 has, for example, the cam prolongation 94 shown in FIG. 12 to FIG. 15 and in FIG. 20. The shaft prolongation 128 may be configured flexibly in the region between the stationary and the movable cleaning element 40s and 40 by means of a directed choice of material and/or by a directed material weakening. Consequently, in the case of too high a cleaning pressure, the movable cleaning element 40 can be deflected in a flexible way with respect to the stationary cleaning element 40s.

The embodiments of the plug-on brush 14 which are illustrated in FIGS. 27 to 32 are in each case configured such that the neck 34 is fixedly connected to the connection piece 32 in a plug-on or releasable manner and therefore does not move together with the movable cleaning elements 40. Preferably, the zones at which the plug-on shaft 116 emerges from the plug-on brush basic body 102 are at least partially surrounded by soft-elastic material. This serves, in turn, as pinch protection and/or for sealing off and mounting. In order to compensate the distances between the stationary and movable cleaning elements 40s, 40, zones consisting of specially configured soft material may be used in all the design variants. These form a resilient buffer preventing a pinching of lips, mouth surfaces, etc. For example, concertina-like bellows consisting of soft material could be formed. Other flexible structures compensating the movement and consisting of soft material may also be envisaged.

Alternatively to the arrangement of the cleaning elements 40, 40s which is shown in FIG. 31 and FIG. 32, it is, of course, also possible to arrange stationary cleaning elements 40s in the free end region of the plug-on brush 14 and to position the movable cleaning element 40 on the neck side. Furthermore, it is also conceivable, by means of two shaft prolongations 128 running parallel to one another, to provide two pivotally movable cleaning elements 40 with different maximum deflection angles or one pivotally movable cleaning element 40 with two different maximum deflection angles. Thus, at least one pivotally movable cleaning element 40 can achieve a higher cleaning performance on account of a larger maximum deflection angle.

It is generally true of all the described embodiments of the plug-on brush 14 that they have a length of 55 mm to 85 mm, preferably of 65 mm to 75 mm, measured from their free end as far as the plug-on side end of the plug-on brush 14. The vent hole 112, opened in the finished plug-on brush 14, is located, in the longitudinal direction, at a distance of 25 mm to 35 mm, preferably of 28 mm to 32 mm, from the plug-on side end of the plug-on brush 14. In the embodiment shown in FIG. 21 to FIG. 25, the snap boss of the spring element 114 is located, in the longitudinal direction, at a distance of between 12 mm and 20 mm, preferably 15 mm and 17 mm, from the plug-on side end of the plug-on brush 14.

The hard material used for the components described above is, for example, polypropylene (PP), polyester (PET), polycyclohexane dimethanol terephthalate (PCT/PCT-A (acid-modified)/PCT-G (glycol-modified)), polyethylene (PE), polystyrene (PS), styreneacrylonitrile (SAN), polymethylmethacrylate (PMMA), acrylobutadienestyrene (ABS), polyoxymethylene (POM) or polyamide (PA). Polypropylene (PP) with a modulus of elasticity of 1000 N/m$^2$ to 2400 N/m$^2$, preferably of 1300 N/m$^2$ to 1800 N/m$^2$, is preferably employed.

The soft-elastic material used is, for example, low-density polyethylene (PE-LD), high-density polyethylene (PE-HD), polyethylene (PE), polyvinylchloride (PVC), elastomeric material, such as polyurethane (PUR), or a thermoplastic elastomer (TPE), preferably a thermoplastic elastomer (TPE). It is also possible to use polyolefin-based elastomer. The Shore A hardness of the soft-elastic material used is preferably below 90.

When soft-elastic material is used on the basic body 10, for example for the adhesive elements 28, or when damping elements are formed, in particular, on the plug-on brush 14, the thickness of layers of soft-elastic material amounts to more than 0.2 mm, preferably to more than 0.5 mm. Soft-elastic material with a Shore A hardness of below 50, preferably of below 35, is employed both on the basic body 10 and on the plug-on brush 14 for the damping of vibrations, oscillations and noise emissions which occur in the active operating state. These material properties offer a good compromise for optimally ensuring the functions which are to be fulfilled by the soft-elastic material. If appropriate, thin layers of soft-elastic material may also be integrally formed in the standing portion 18 or above lettering fields.

Furthermore, soft-elastic material is also used to form cleaning elements arranged on the head 38 or on the cleaning element 40, such as a tongue cleaner, already mentioned, or soft-elastic cleaning lamellae. The soft-elastic cleaning lamellae may in this case be arranged around the bristles 42 on the outside or within bristle fields. The bristles 42 themselves are preferably manufactured from polyamide or polyester with a diameter of 0.1 to 0.2 mm, preferably of 0.125 mm to 0.175 mm. They are arranged in bristle bundles. The head 38, having a relatively small shape, has 20 to 30, preferably 22 to 28 bundles of bristles 42. Various shapes of bristle arrangements are shown in the following FIGS. 33 to 41.

The embodiments, shown in FIGS. 33 and 34, of cleaning elements 40 arranged on heads 38 are suitable, in particular, for electric toothbrushes 12 which generate a reversibly pivoting or reversibly translational movement of the cleaning elements 40 in the active operating state. In a similar way to the remarks regarding the tongue cleaner, preferably some of the cleaning elements 40 are oriented transversely with respect to the direction of movement. This applies particularly to elongate bristle bundles, of which the longitudinal extent, as seen in a top view of the top side 24, is greater than their transverse extent, or to elongate lamella-like cleaning elements 40 consisting of soft material. In both embodiments shown, bristles 42 are combined into bristle bundles above elongately rounded, sickle-shaped, C-shaped, crescent-shaped or oval base areas. By the elongately arranged bristle bundles being oriented with their longitudinal axis at least virtually parallel to the pivot axis of the cleaning elements 40, a wipe-like effect is achieved by means of a reversible pivoting movement. Moreover, particularly in the embodiment in FIG. 34, bristle bundles are also arranged with their longitudinal axis at right angles to the longitudinal axis of the neck 34, in order to achieve such a wiping effect also in the case of a reversibly translational to-and-fro movement of the head 38. The embodiment, shown in FIG. 34, of a movable cleaning element 40 is therefore also suitable particularly for a combined movement of the cleaning element 40 with a reversibly pivoting and a reversibly translational movement component. The embodiments of cleaning elements 40, as shown, may, of course, also be used in manual toothbrushes. In manual use, similar cleaning movements, naturally with a much lower frequency, are employed.

The movable cleaning elements 40 shown in FIGS. 35 to 38 are arranged above an essentially circular or longitudinally slightly elliptically shaped bristle carrier 120 and are provided, in particular, for use in the case of reversibly oscillating forms of movement (cf. FIG. 4 and FIG. 26). In addition to circular bristle bundles, these cleaning elements 40 are also arranged with bristles 42 above essentially elongate base areas (see FIG. 35, FIG. 36) or even sickle-shaped base areas (see FIG. 37 and FIG. 38). In this case, too, the longitudinal axes of the elongate base areas of the bristle bundles are preferably arranged at least virtually at right angles to the pivot axis about which the cleaning element 40 oscillates reversibly.

Figure 39:
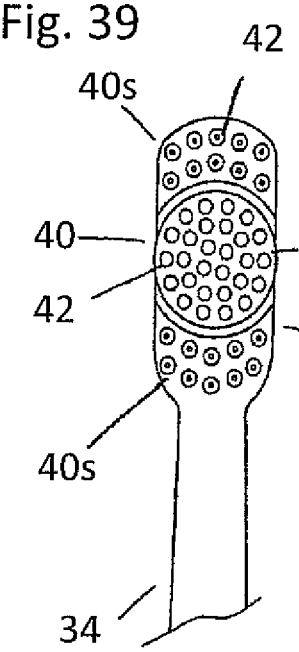
FIG. 39-FIG. 41 show top views of the top sides of heads of various embodiments of plug-on brushes with reversibly oscillatable cleaning elements and with further cleaning elements arranged stationarily with respect to the neck.
Figure 40:
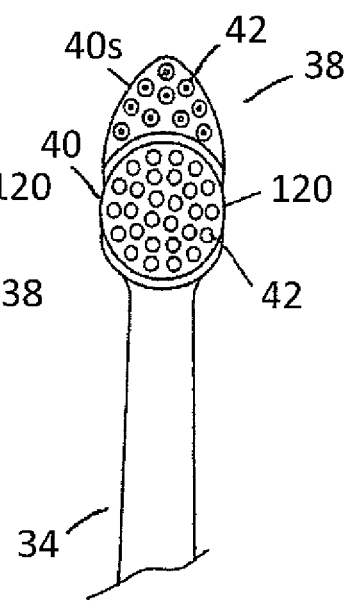
Figure 41:
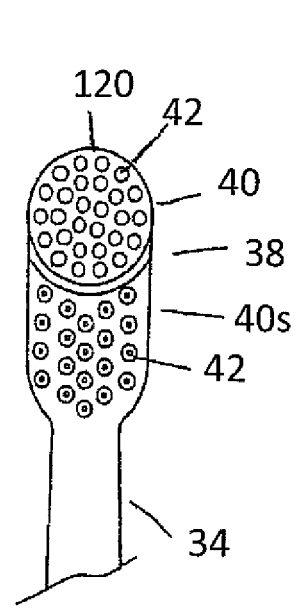

FIGS. 39 to 41 show embodiments of cleaning elements 40 in which in each case stationary cleaning elements 40s are combined with pivotally movable cleaning elements 40. Thus, for example in FIG. 39, a centrally arranged, pivotally movable cleaning element 40 on a circular bristle carrier 120 is surrounded both at the free end region and on the neck side of the head 38 by stationary cleaning elements 40s. In the embodiment shown in FIG. 40, the reversibly oscillatable cleaning element 40 is adjacent to a stationary cleaning element 40s which is arranged at the free end region of the head 38 and has a round triangular base area. In FIG. 41, a stationary cleaning element 40s is arranged only on the neck side of the pivotally movable cleaning element 40. Movable cleaning elements 40 according to FIGS. 35 to 38 may, of course, also be combined with the cleaning elements 40, 40s shown in FIGS. 39-41.

The bristling of the embodiments of cleaning elements 40, as shown, may take place in various ways, for example by means of conventional small anchor plates or, as already mentioned, by means of IMT or AFT methods. Particularly in the case of the two last-mentioned methods, it is possible to produce bristle bundles with sickle-shaped, C-shaped, S-shaped, octagonal, polygonal, circular, oval, etc. base areas which are shaped symmetrically or even asymmetrically. These bristle bundles having comparatively large extents of the base areas in various directions combine the wipe-like effects for various directions of movement of the cleaning elements 40. Moreover, the two bristling methods allow a higher freedom of configuration with regard to the appearance of the bristle field.

In addition to bristles 42 or bundles of bristles 42 rising essentially at right angles from the bristle carrier 120, it is also possible to form bristles 42 which are arranged in an X-shaped manner on a cleaning element 40, 40s. The bristles 42 oriented in the form of an X are then at an angle of 3° to 20°, preferably of 8° to 14°, to one another. Moreover, it is possible to arrange bristles 42 or bristle bundles with longer and/or pointed bristles 42 in particular onto outer margins of the cleaning elements 40, 40s.

These then serve, in particular, for an improved cleaning of the interdental spaces between the teeth. Furthermore, it is also possible to assemble the cleaning elements 40 with bristles 42 on essentially round or slightly oval base areas into bristle bundles which then serve, in particular, for cleaning the gum edge. Overall, cylindrical and also one-sidedly or two-sidedly pointed bristles 42 may be used on the bristle carriers 120, in each case of the same type or combined or else in combination with additional massaging and cleaning lamellae or cleaning structures consisting of soft material. The use of pointed bristles 42 on electric toothbrushes is already described in detail and reference in WO 2004/093718. The described heads or cleaning elements and production methods may be combined directly with the electric toothbrush 12 according to the invention.

The plug-on brushes 14 described preferably have an exchangeable configuration. It is also possible, however, to configure an electric toothbrush 12 with the transmission 48 according to the invention and with the plug-on brush 14 such that these elements are formed in one piece and the plug-on brush 14 is not exchangeable. This is the case, above all, in advantageous battery-operated appliances.

For the sake of completeness, it may also be mentioned that the cleaning elements 40, 40s shown by way of example may also be exchanged for other cleaning or operative elements. In oral hygiene, these are, for example, generally interdental attachments, such as spiral brushes, toothpicks, etc., polishing elements, soft-elastic elements (for example, proficups) or tongue cleaner attachments. The transmission 48 according to the invention may, of course, also be employed in other areas of body care (face massage, nail care, head massage, wet and dry shaving, etc.) with correspondingly designed operative attachments.

FIG. 42 shows a detail of the interior of a further embodiment of an electric toothbrush 12 according to the invention. The detail corresponds approximately to the illustration shown in FIG. 5 in connection with a previously described embodiment. Identical parts in FIG. 42 are given the same reference symbols as in FIG. 5. In contrast to the embodiment shown in FIG. 5, in the embodiment in FIG. 42 the transmission 48 is equipped only with a single transmission stage. This transmission stage is formed by a cam 72 and a further pick-up 132. The cam 72 is fastened fixedly in terms of rotation on the drive shaft 60, not shown in FIG. 42, of the electric motor 58. In contrast to the embodiment in FIG. 5, the transmission 48 has no drive gearwheel 68 and no contrate wheel 70. On account of the consequently reduced number of transmission elements and therefore the absence of gearwheel transmission, in this embodiment the transmission 48 makes less noise during operation and is simpler and more cost-effective to produce. The energy consumption and the preferred movement patterns (including movement frequency, deflection and angle of rotation) may be adopted essentially in a similar way from the embodiments described previously.

In a similar way to the embodiment shown in FIG. 5, the embodiment illustrated in FIG. 42 also has a control unit 52, arranged laterally with respect to the electric motor 58, for controlling the operating states of the electric motor 58 and also an internal framework 46 for fixing the further pick-up 132 together with the output shaft 30 in position with respect to the cam 72. In this case, in the axial direction, parallel to the longitudinal axis of the output shaft 30, the pick-up 132 is supported in its position, on the one hand, by a head bearing 134 of the internal framework 46 and, on the other hand, with respect to the electric motor 58, by a stabilizing shaft.

As may be gathered from FIGS. 43 and 44, the output shaft 30 runs in a parallel offset to the drive shaft 60 indicated in the figures as a dashed line. If, in contrast to the embodiments shown, a parallel shaft offset between the shafts 30 and 60 is not desired, this may be compensated by a correspondingly intermediate spur gear with at least two gearwheels, the first gearwheel of which is seated, for example, on the drive shaft 60 and engages into a second gearwheel, to which the cam 72 is attached.

In the embodiment illustrated in FIG. 42, the drive shaft 60 is positioned parallel, but not coaxially, to the output shaft 30. In order to arrange the plug-on brush 14 at an angle to the basic body 10, the drive shaft 60 and the output shaft 30 must also form the same angle. For ergonomic reasons, an angle smaller than 20°, preferably smaller than 10°, is preferred. In this design variant, the internal framework 46 is modified, as compared with the variant illustrated in FIG. 42, so that the output shaft 30, the output shaft sleeve 75 and the pick-up 74, 132 stand at said angle to the drive shaft 60. An illustration of this variant is shown in FIGS. 53 to 56.

As described above, the further pick-up 132 is positioned or fixed along its longitudinal direction by a stabilizing shaft 136. Alternatively, however, a pick-up extension, as it is known, may also be formed, which prolongs the further pick-up 132 in the direction of the electric motor 58 and supports it on the latter. This form of guidance of the further pick-up 132 is described further in connection with FIGS. 53 to 56.

The illustration of FIG. 44 shows particularly clearly how a closed-continuous pick-up surround 142 of the further pick-up 132 surrounds the cam 72 radially with slight play. The pick-up surround 142 is equipped radially on the inside, opposite the outer wall of the cam 72, with a sensing wall 144. If, then, in the active operating state of the electric motor 58, the cam 72 is set in rotation about the drive shaft 60, the outer wall of the cam 72 slides along the sensing wall 144 of the pick-up surround 142 and the further pick-up 132, together with its output shaft 30, moves in a reversibly pivoting manner about the latter. The play between the sensing wall 144 and the cam 72 and, where appropriate, the use of elastic materials prevents a "knocking" of the output shaft 30 and damage to the electric motor 58 under high loads during cleaning. It is also possible to design the pick-up surround 142 to be open on one side too, that is to say fork-like, in order to give it higher elasticity and thereby avoid said "knocking". The friction of the cam 72 against the sensing wall 144 can be reduced, using suitable lubricants. Likewise in order to reduce the friction, it is possible to shape the cam 72 in a slightly crowned manner and reduce the size of the sliding surface by means of an edge-like configuration of the sensing wall 144. The crowning is described in detail in connection with FIG. 49.

FIGS. 45 to 48 show various perspective views of the further pick-up 132. As mentioned above, the pick-up surround 142 and, furthermore, a pick-up recess 148 are shaped on a pick-up body 146. Said elements 132, 146, 142 are preferably produced from a hard plastic material by an injection molding method. The output shaft 60 arranged fixedly in terms of rotation on the pick-up body 146 is preferably manufactured from a metal, for example from a stainless steel.

Figure 46:
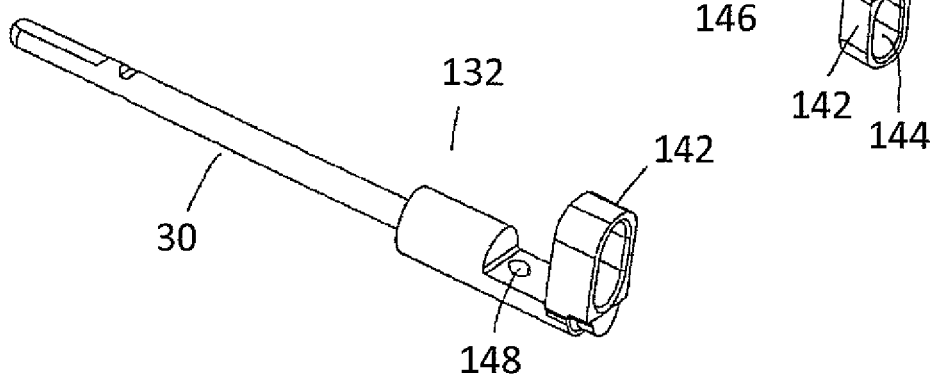
Figure 47:
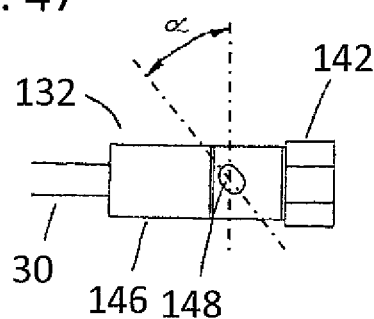
Figure 48:
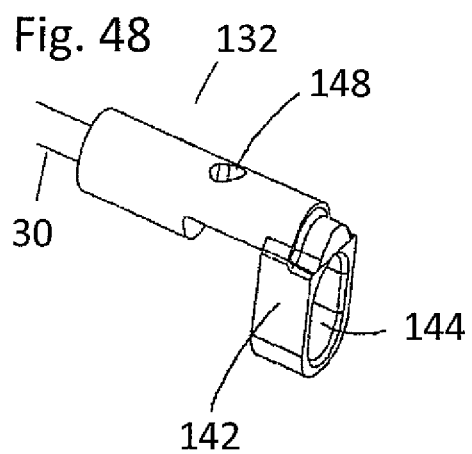
Figure 53:
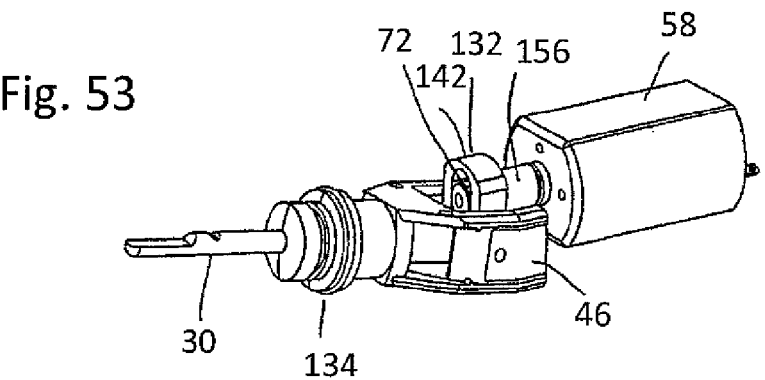
FIG. 53 shows a perspective view of the interior of a further embodiment of the electric toothbrush according to the invention, in which the drive shaft and the output shaft run at an inclination with respect to one another.
Figure 54:
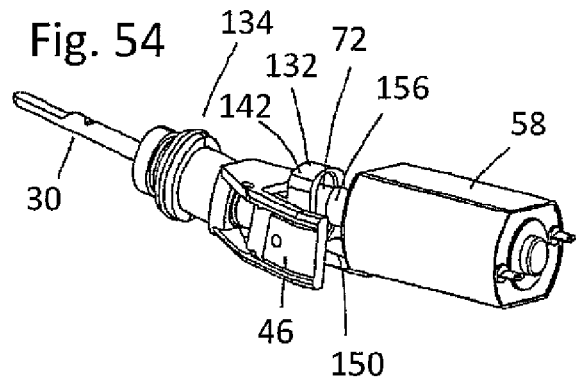
FIG. 54 shows a further perspective view of the interior shown in FIG. 53.
Figure 55:
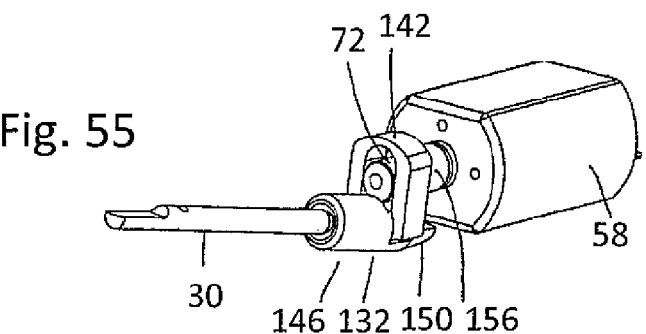
FIG. 55 shows a further perspective view of the interior shown in FIGS. 53 and 54, without the internal framework being illustrated.
Figure 56:
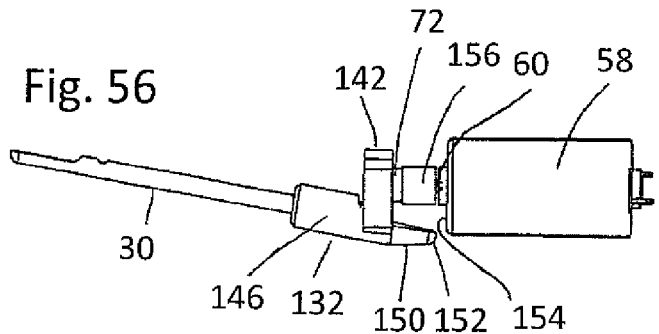
FIG. 56 shows a side view of the interior shown in FIGS. 53 to 55, without the internal framework being illustrated.

As shown in FIGS. 46 to 48, for the already abovementioned positive guidance of the further pick-up 132, the pick-up recess 148 is shaped on that side of the pick-up body 146 which lies opposite the pick-up surround 142. A pin, in the form of the stabilizing shaft 136, which projects fixedly on the internal framework 46 in the direction of the further pick-up 132, engages with play into this pick-up recess 148. The stabilizing shaft 136 can be seen in FIGS. 42 and 43. It is, of course, also possible to provide a corresponding recess on the internal framework 46 and to arrange the pin on the further pick-up 132.

Figure 45A:
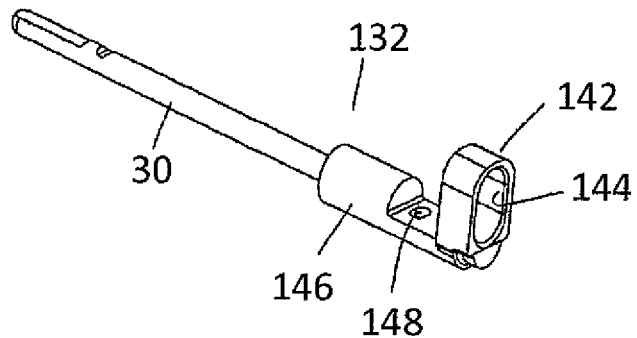
FIGS. 45a, 45b and 46-48 show various views of a further pick-up of the transmission for the embodiment, shown in FIGS. 42 to 44, of the electric toothbrush according to the invention.
Figure 45B:
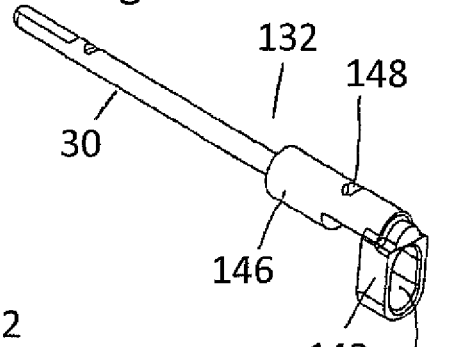

In the embodiment shown in FIGS. 45a and 45b, the pick-up recess 148 has an essentially cylindrical or oval configuration and is equipped with an inside diameter which allows a reversible pivoting movement of the further pick-up 132 about the longitudinal axis of the output shaft 30 and at the same time prevents a displacement of the further pick-up 132 in the longitudinal direction. On account of this pick-up recess 148, in cooperation with the stabilizing shaft 136, the abovementioned pick-up extension becomes superfluous and is no longer required.

By contrast, in the embodiment shown in FIGS. 47 and 48, the pick-up recess 148 is designed in the manner of a long hole, so that a positive guidance of the further pick-up 132 in the manner of a cam gear in the longitudinal direction is additionally brought about. If, then, in an active operating state of the electric motor 58, the further pick-up 132 moves in a reversibly pivoting manner about the longitudinal axis of the output shaft 30, then at the same time this generates a reversibly translational to-and-fro movement component of the pick-up 132 in the longitudinal direction of the output shaft 30.

The maximum longitudinal displacement during the reversibly translational to-and-fro movement component of the output shaft 30 is determined by a pitch angle $\alpha$, formed between the longitudinal axis of the pick-up recess 148 and a transverse axis running at right angles with respect to the longitudinal axis of the output shaft 30, and the maximum rotary angle $\theta$ of the output shaft 30. The pitch angle $\alpha$ is preferably fixed at lower than 45°, particularly preferably at between 10° and 30°. The resulting maximum longitudinal displacement during the reversibly translational to-and-fro movement amounts to less than 2 mm, preferably to less than 1 mm. In the linear shaping of the pick-up recess 148 in the manner of a long hole, as illustrated in FIGS. 47 and 48, a step-up ratio between the reversible pivoting movement component and the reversibly translational to-and-fro movement component of 1:1 is achieved. The superposition of the reversibly pivoting and the reversibly translational movement component leads to a closed path of movement of the cleaning element 40 connected to the output shaft 30. Depending on the configuration of the recess 148, various movement patterns can be generated. With regard to further possibilities for generating movement patterns of various types, reference may again be made at this juncture to FIGS. 16 to 20 and to the table in the text. The shape of the recess 148 is not in this case restricted to that shown in FIG. 47, but may also have an S-shaped or C-shaped configuration or another non-straight curved shape. For example, wavy shapes may also be envisaged, with the aid of which even higher step-up ratios of the pivoting movement component to the translational movement component can be achieved.

FIGS. 49 and 50 illustrate two embodiments of cams 72 by way of example. The cam 72 shown in FIG. 49 has an essentially cylindrical configuration, its longitudinal mid-axis running parallel, and offset, to the longitudinal mid-axis of the drive shaft 60 (indicated by dashed lines). The cam 72 is therefore arranged eccentrically with respect to the drive shaft 60. The relation, resulting when a cam 72 shaped in this way is used, between the deflection angle $\phi$ of the output shaft 30 and the rotary angle $\theta$ of the drive shaft 60 (or the time t) is illustrated in the case of one complete revolution of 360° ($2\pi$) in FIG. 51. This functional relation corresponds to the profile shown in FIG. 16 and gives rise to a 1:1 step-up of the rotational movement of the drive shaft 60 into the reversibly pivoting movement of the pick-up 132 or of the output shaft 30.

The deflection angle $\phi$ in this case follows a sinusoidal profile and, in terms of amount, assumes maximum values as a function of the eccentricity of the arrangement of the cam 72 with respect to the drive shaft 60 and of the diameter of the cam 72. The 1:1 step-up is used, above all, in connection with an electric motor 58, for the high rotational speeds already described above.

The cam 72 has a crowned shape, that is to say its outer surface is curved slightly outward and does not run parallel to the outer surface of the drive shaft 60. In other words, the diameter of the cam 72 changes along the longitudinal extent of the cam 72 and gives rise to this special shape. The cam 72 possesses at its ends a diameter of 4.5 mm to 5.5 mm, preferably of 4.9 mm to 5.1 mm, while in the mid-plane it possesses a maximum diameter of 5 mm to 6 mm, preferably of 5.2 mm to 5.4 mm. The crowned surface has a radius of curvature of between 95 mm and 115 mm, preferably of between 100 mm and 110 mm. The ratio of the radii of curvature in the end region of the cam 72 to one of these radii amounts in terms of the diameter at the end to the diameter in the mid-plane to 1.01:1 to 1.3:1, preferably 1.02:1 to 1.1:1.

The crowning of the cam 72 has the effect that, in the active operating state, less friction occurs between the cam 72 or its outer surface and the further pick-up 132. This likewise entails a noise reduction. The crowning is not necessarily required for the functionality of the transmission 48. It is illustrated by way of example in FIG. 49a and FIG. 49b. The cam 72 shown in FIG. 50 is not equipped with a crowning.

The distance between the longitudinal mid-axis of the cam 72 and the longitudinal mid-axis of its drive shaft 60 functioning as an axis of rotation amounts to 0.1 mm to 0.6 mm, preferably to between 0.2 mm and 0.45 mm. This distance is a measure of the eccentricity or unbalance of the cam 72 which, during its rotation, causes the deflection of the further pick-up 132. The distance between the longitudinal mid-axes of the drive shaft 60 and of the output shaft 30 amounts to between 3 mm and 9 mm, preferably to between 5 mm and 7 mm, particularly preferably to about 6 mm.

The ratio of the distances of the longitudinal mid-axes, on the one hand, from the output shaft 30 to the drive shaft 60 in the region of the pick-up 74, 132, and, on the other hand, from the drive shaft 60 to the cam 72 arranged eccentrically on it amounts to 5:1 to 90:1, preferably to at least 10:1, particularly preferably to 11:1 to 35:1. This results in a small maximum (or full) deflection angle $\phi_{total}$ of the output shaft 30 between outermost deflection positions of about 1° to 23°, preferably of about 3° to 15°, particularly preferably of about 5° to 12°. This small maximum deflection angle $\phi_{total}$ gives rise, in turn, to a low deflection of the cleaning elements 40, which, in interaction with the high rotational speed of the electric motor 58, ensures a particularly effective and careful cleaning of the teeth and of the gums.

When an electric motor 58 of lower rotational speed is used, the step-up ratio may be increased, for example, by means of the cam 72 shown in FIGS. 50 and 52, in order to achieve a higher frequency of movement of the movable cleaning element 40. This embodiment of the cam 72 is arranged centrically with respect to the drive shaft 60. The cam 72 has a rounded, essentially triangular cross-sectional shape. It corresponds in shape and function to the cam 72 already shown in FIG. 10 and FIG. 17, but, in this embodiment, is fastened directly on the drive shaft 60. As may be gathered from the functional dependence, shown in FIG. 52, of the deflection angle $\phi$ of the output shaft 30 on the rotary angel $\theta$ of the drive shaft 60 (or the time t) for one complete revolution of the drive shaft 60 of 360° ($2\pi$), a step-up of 1 to 3 is implemented by means of this cam 72, that is to say, during one revolution of the drive shaft 60, three complete pivoting movement cycles of the output shaft 30 are executed.

FIGS. 53 to 56 illustrate a further embodiment of a transmission 48 according to the invention, in which the drive shaft 60 is arranged at an inclination with respect to the output shaft 30. The further pick-up 132 is supported along its longitudinal direction by a pick-up extension 150, already mentioned, and the head bearing 134. The pick-up extension 150 is configured so as to taper conically toward its free end region. A pick-up extension tip 152 is thus shaped, which stands virtually in a punctiform manner on a supporting surface 154 assigned to the electric motor 58 or provided on the inside of the basic body 10. The pick-up extension tip 152 is in this case preferably shaped as a continuation of the longitudinal mid-axis of the output shaft 30, so that, in the active operating state of the electric motor 58, only point rotation about a bearing point of the pick-up extension tip 152 on the supporting surface 154 is obtained. By means of suitable measures, for example the application of a lubricant or the selection of suitable materials for the pick-up extension tip 152 and the supporting surface 154, friction which occurs in this case can be reduced. Moreover, it is also possible, by virtue of positive guidance, produced in interaction with the internal framework 46, by means of the stabilizing shaft 136, also to dispense entirely with putting the pick-up extension tip 152 in place on the supporting surface 154. In FIGS. 53 to 56, the cam 72 is arranged fixedly in terms of rotation on a cam carrier 156.

The angle which is formed between the plug-on brush 14 and the basic body 14 is the same as that which is formed between the drive shaft 60 and the output shaft 30. For ergonomic reasons, this angle amounts to less than 20°, preferably to less than 10°. In this design variant, the internal framework 46 is modified, as compared with the variant illustrated in FIG. 42, so that the output shaft 30, the output shaft sleeve 75 and the further pick-up 132 stand at said angle to the drive shaft 60.

It is, of course, also possible to use for a single-stage transmission 48 all the cams 72, described in connection with a multistage transmission 48, as they are shown, for example, in FIGS. 8 to 20. In particular, these cams 72 may have cross sections in the form of rounded n-sided polygons, n being an odd positive number. All the other features of the above-described embodiments of electric toothbrushes 12, according to the invention, may also be transferred to the embodiment shown in FIGS. 42 to 56.

What is claimed is:

1. An electric toothbrush comprising:
    a basic body, a grip, an electric motor, a gear, a transmission; and
    a plug-on brush including a plug-on brush body having a neck body and a head arranged at a first end of the neck, at least one movable cleaning element connected fixedly in terms of rotation to a shaft prolongation, and at least one stationary cleaning element attached to the head; wherein
        the transmission converts the rotational movement provided by the electric motor into a reversing pivoting movement at an output shaft;
        the plug-on brush body is removably attachable to, but impivotable with respect to the basic body of the electric toothbrush at a second end of the neck; and
        the shaft prolongation is arranged in and pivotally movable relative to the plug-on brush body, and is removably and operatively connected to the output shaft, such that the reversing pivoting movement of the output shaft transmitted via the shaft prolongation causes the at least one movable cleaning element to move relative to the at least one stationary cleaning element in a lateral pivoting movement about the longitudinal axis of the shaft prolongation.

2. The electric toothbrush of claim 1, further comprising a plurality of stationary cleaning elements and a plurality of movable cleaning elements arranged to alternate along the longitudinal axis of the plug-on brush.

3. The electric toothbrush of claim 2, wherein bristles are arranged on the at least one movable cleaning element and the at least one stationary cleaning element, and the bristles on the at least one stationary cleaning element are shorter than the bristles on the at least one movable cleaning element.

4. The electric toothbrush of claim 1, wherein the at least one moveable cleaning element is arranged on a shaft being movable inside the plug-on brush body and which emerges from the plug-on brush body at a zone.

5. The electric toothbrush of claim 4, wherein the zone is at least partially surrounded by soft-elastic material.

6. The electric toothbrush of claim 4, wherein the at least one movable cleaning element is inclined relative to the plug-on shaft.

7. The electric toothbrush of claim 1, wherein the at least one stationary cleaning element is arranged in a region on the head opposite from the neck.

8. The electric toothbrush of claim 7, wherein the at least one movable cleaning element is arranged in a region on the head next to the neck.

9. The electric toothbrush of claim 1, wherein the at least one movable cleaning element is arranged in a region on the head opposite from the neck.

10. The electric toothbrush as claimed in claim 9, wherein the stationary cleaning element is arranged in a region on the head next to the neck.

11. The electric toothbrush of claim 1, wherein the shaft prolongation extends axially along the longitudinal axis of the neck from the at least one movable cleaning element.

12. The electric toothbrush of claim 1, wherein the electric motor rotates at a rotational speed of between 3000 rev/min and 8000 rev/min during the no-load operation of the electric toothbrush.

13. The electric toothbrush of claim 1, wherein the at least one movable cleaning element moves in a reversing pivoting manner at a frequency of between 3000 rev/min and 15000 rev/min.

14. The electric toothbrush of claim 1, wherein at least one further pivoting movement is superposed on the pivoting movement of the at least one movable cleaning element.

15. The electric toothbrush of claim 1, wherein the movement of the at least one movable cleaning element has a reversibly translational to-and-fro movement component in a direction virtually parallel to the longitudinal axis of the neck.

16. The electric toothbrush of claim 1, wherein the distance between the at least one stationary cleaning element and the at least one movable cleaning element is sufficient to allow the movement of the at least one movable cleaning element to include both a reversing pivoting movement and a translational to-and-fro movement.

17. The electric toothbrush of claim 16, wherein the reversibly translational to-and-fro movement component has a frequency of between 1000 rev/min and 12000 rev/min.

18. The electric toothbrush of claim 1, wherein the at least one movable cleaning element includes at least one of: a bundle of bristles having an elongate cross section, a bundle of elongate elastomeric cleaning lamellae, or cleaning structures which are oriented with their longitudinal axis transverse to the direction of movement of the at least one movable cleaning element.

19. The electric toothbrush of claim 1, wherein the basic body comprises a plug-on portion for mechanically coupling the plug-on brush to the electric toothbrush basic body, and the electric toothbrush basic body further comprises a connection piece for the rotationally-fixed reception of the plug-on brush.

20. The electric toothbrush of claim 1, wherein the length of the plug-on brush in the longitudinal direction is between 65 mm to 75 mm.

21. An electric toothbrush comprising:
a basic body, a grip, an electric motor, a gear, a transmission; and
a plug-on brush including a plug-on brush body having a neck and a head arranged at a first end of the neck, a plurality of movable cleaning elements connected fixedly in terms of rotation to a shaft prolongation, and a plurality of stationary cleaning elements; wherein
the transmission converts the essentially continuous rotational movement provided by the electric motor into a reversing pivoting movement at an output shaft;
the plug-on brush body is removably attachable to, but impivotable with respect to the basic body of the electric toothbrush at a second end of the neck;
the shaft prolongation is arranged in and pivotally movable relative to the plug-on brush body, and is removably and operatively connected to the output shaft, such that the reversing pivoting movement of the output shaft transmitted via the shaft prolongation causes the plurality of movable cleaning elements to move relative to the plurality of stationary cleaning elements in a lateral pivoting movement about the long axis of the shaft prolongation; and
at least a portion of the plurality of stationary cleaning elements and at least a portion of the plurality of movable cleaning elements are arranged to alternate along the longitudinal axis of the plug-on brush.

22. An electric toothbrush comprising:
a basic body, a grip, an electric motor, a gear, a transmission; and
a plug-on brush including a plug-on brush body having a neck and a head arranged at a first end of the neck, a plurality of movable cleaning elements connected fixedly in terms of rotation to a shaft prolongation, and a plurality of stationary cleaning elements; wherein
the transmission converts the essentially continuous rotational movement provided by the electric motor into a reversing pivoting movement at an output shaft;
the plug-on brush body is removably attachable to, but impivotable with respect to the body of the electric toothbrush at a second end of the neck;
the shaft prolongation is arranged in and pivotally movable relative to the plug-on brush body, and is removably and operatively connected to the output shaft, such that the reversing pivoting movement of the output shaft transmitted via the shaft prolongation causes the plurality of movable cleaning elements to move relative to the plurality of stationary cleaning elements in a lateral pivoting movement about the longitudinal axis of the shaft prolongation; and
at least one movable cleaning element is arranged in a region on the head opposite from the neck.

23. The electric toothbrush of claim 22, wherein at least one stationary cleaning element is arranged in a region on the head next to the neck.

24. An electric toothbrush comprising:
a basic body, a grip, an electric motor, a gear, a transmission; and
a plug-on brush including a plug-on brush body having a neck and a head arranged at a first end of the neck, a plurality of movable cleaning elements connected fixedly in terms of rotation to a shaft prolongation, and a plurality of stationary cleaning elements; wherein
the transmission converts the essentially continuous rotational movement provided by the electric motor into a reversing pivoting movement at an output shaft;
the plug-on brush body is removably attachable to, but impivotable with respect to the body of the electric toothbrush at a second end of the neck;
the shaft prolongation is arranged in and pivotally movable relative to the plug-on brush body, and is removably and operatively connected to the output shaft, such that the reversing pivoting movement of the output shaft transmitted via the shaft prolongation causes the plurality of movable cleaning elements to move relative to the plurality of stationary cleaning elements in a lateral pivoting movement about the longitudinal axis of the shaft prolongation;
the plurality of movable cleaning elements and the plurality of stationary cleaning elements have bristles, and
the bristles on the movable cleaning elements are longer than the bristles on the stationary cleaning elements.

* * * * *